United States Patent
Kumada et al.

(10) Patent No.: US 9,789,335 B2
(45) Date of Patent: Oct. 17, 2017

(54) MGF$_2$—CAF$_2$ BINARY SYSTEM SINTERED BODY FOR RADIATION MODERATOR AND METHOD FOR PRODUCING THE SAME

(71) Applicants: UNIVERSITY OF TSUKUBA, Ibaraki (JP); TECHNO EYE CORPORATION, Kyoto (JP); DAICO MFG CO., LTD., Kyoto (JP)

(72) Inventors: Hiroaki Kumada, Ibaraki (JP); Tetsuyuki Nakamura, Kyoto (JP); Takeshi Ikeda, Kyoto (JP); Takuji Shigeoka, Kyoto (JP)

(73) Assignees: TECHNO EYE CORPORATION, Kyoto (JP); DAICO MFG CO., LTD., Kyoto (JP); UNIVERSITY OF TSUKUBA, Ibaraki (JP)

( * ) Notice: Subject to any disclaimer, the term of this patent is extended or adjusted under 35 U.S.C. 154(b) by 122 days.

(21) Appl. No.: 14/684,765

(22) Filed: Apr. 13, 2015

(65) Prior Publication Data
US 2016/0082282 A1   Mar. 24, 2016

(30) Foreign Application Priority Data

Sep. 24, 2014   (JP) ................. 2014-193899

(51) Int. Cl.
| | |
|---|---|
| *A61N 5/10* | (2006.01) |
| *C04B 35/553* | (2006.01) |
| *C04B 35/64* | (2006.01) |
| *C04B 35/626* | (2006.01) |
| *G21F 1/00* | (2006.01) |
| *G21K 1/00* | (2006.01) |

(52) U.S. Cl.
CPC .............. *A61N 5/10* (2013.01); *C04B 35/553* (2013.01); *C04B 35/6261* (2013.01); *C04B 35/62685* (2013.01); *C04B 35/64* (2013.01); *G21F 1/00* (2013.01); *G21K 1/00* (2013.01); *A61N 2005/109* (2013.01); *A61N 2005/1098* (2013.01); *C04B 2235/3206* (2013.01); *C04B 2235/3208* (2013.01); *C04B 2235/449* (2013.01); *C04B 2235/5436* (2013.01); *C04B 2235/5481* (2013.01); *C04B 2235/604* (2013.01); *C04B 2235/656* (2013.01); *C04B 2235/658* (2013.01); *C04B 2235/6567* (2013.01); *C04B 2235/6583* (2013.01); *C04B 2235/661* (2013.01); *C04B 2235/77* (2013.01); *C04B 2235/96* (2013.01)

(58) Field of Classification Search
CPC ................ C04B 35/553; G21F 1/08
See application file for complete search history.

(56) References Cited

U.S. PATENT DOCUMENTS

| | | | | |
|---|---|---|---|---|
| 4,131,820 | A | * | 12/1978 | Washida ................. H01J 9/233 313/377 |
| 2014/0079902 | A1 | † | 3/2014 | Fujiwara |

FOREIGN PATENT DOCUMENTS

| | | |
|---|---|---|
| EP | 1 895 819 | 3/2008 |
| EP | 1895819 A1 † | 3/2008 |
| EP | 2 865 658 | 4/2015 |
| EP | 2 927 202 | 10/2015 |
| EP | 3 059 216 | 8/2016 |
| JP | 2000-086344 | 3/2000 |
| JP | 2000-302553 | 10/2000 |
| JP | 2000-302553 A1 † | 10/2000 |
| JP | 2004-083362 | 3/2004 |
| JP | 2004-233168 | 8/2004 |
| JP | 2008-36143 | 2/2008 |
| JP | 2009-192488 | 8/2009 |
| JP | 2009-204428 | 9/2009 |
| JP | 2012-121776 | 6/2012 |
| JP | 2012-206913 | 10/2012 |
| JP | 5112105 | 1/2013 |
| JP | 5711511 B2 † | 4/2015 |
| WO | 94/29881 | 12/1994 |
| WO | 2012165334 A1 † | 12/2012 |

OTHER PUBLICATIONS

European Search Report dated Jan. 28, 2016 in corresponding European patent application No. 15163612.3.
Communication dated Feb. 15, 2016 in corresponding European patent application No. 15163612.3.
European Search Opinion dated Feb. 15, 2016 in corresponding European patent application No. 15163612.3.
Zhi Guanglin et al., "Effects of Sintering Additives on Preparation of CaF$_2$ Transparent Ceramics", Journal of Withan University of Technology—Mater. Sci. Ed. Dec. 2011.
Claim 1 Analysis from the Examining Division regarding Third party observation filed in EP 15163612.3.
Claim 2 Analysis from the Examining Division regarding Third party observation filed in EP 15163612.3.
Observations filed in European Patent Application No. 15163612.3 dated Oct. 19, 2016.
S.C. Hu et al. "Pre-Eutectic Densification in MgF$_2$—CaF$_2$", Ceramics International, vol. 9, No. 4, 1983.
Yutaka Shiraishi et al., "On the Molar Volume of MgF$_2$—Ca—F$_2$ Binary System in Solid and Liquid States", G.J. Janz: Molten Salts Handbook, (1967), 46, Academic Press.

(Continued)

*Primary Examiner* — Peter F Godenschwager
(74) *Attorney, Agent, or Firm* — Wenderoth, Lind & Ponack, L.L.P.

(57) ABSTRACT

A MgF$_2$—CaF$_2$ binary system sintered body for a radiation moderator having a compact polycrystalline structure excellent in radiation moderation performance, especially neutron moderation performance, comprises MgF$_2$ containing CaF$_2$ from 0.2% by weight to 90% by weight inclusive, having a bulk density of 2.96 g/cm$^3$ or more, and a bending strength of 15 MPa or more and a Vickers hardness of 90 or more as regards mechanical strengths.

7 Claims, 7 Drawing Sheets

(56) References Cited

OTHER PUBLICATIONS

J.G. Fantidis et al., "Optimised BNCT facility based on a compact D-D neutron generator", International Journal of Radiation Research, vol. 11, No. 4, Oct. 2013.
"Development of Accelerator Type Neutron Capture Therapy System Using New Material Target Technology for Recurrent Cancer Therapy", Report of Research Products (Summary Version), Feb. 25, 2013 with English translation.
Abstract of meeting of Japan Society of Powder and Powder Metallurgy, Autumn Meeting 1998, with English translation.
Annex to Communication issued Nov. 14, 2016 in corresponding European patent application No. 15163612.3.
Communication pursuant to Article 94(3) EPC issued Nov. 14, 2016 in corresponding European patent application No. 15163612.3.
H. Tanaka et al., "Experimental Verification of Bean Characteristics for Cyclotron-Based Epithermal Neutron Source (C-BENS)", Applied Radiation and Isotopes, vol. 69, pp. 1642-1645, 2011.
M. Imoto et al., "Evaluation for Activities of Component of Cyclotron-Based Epithermal Neutron Source (C-BENS) and the Surface of Concrete Wall in Irradiation Room", Applied Radiation and Isotopes, vol. 69, pp. 1646-1648, 2011.
H. Kumada et al., "Dosimetry for Neutron Capture Therapy in JRR-4", Health Physics, vol. 42, No. 1, pp. 23-37, 2007.
S.C. Hu & L.C. De Jonghe, "Pre-Eutectic Densification in $MgF_2$—$CaF_2$," Ceramics International, vol. 9, No. 4, pp. 123-126, 1983.†
Abstract of "On the Molar Volume of the $MgF_2$—$CaF_2$ Binary System in Solid and Liquid States" by Yutaka Shiraishi & Shunroku Watanabe, Bulletin of the Research Institute of Mineral Dressing and Metallurgy, Tohoku University, vol. 34, No. 1, Jun. 1978.†
J. G. Fantidis et al, "Optimised BNCT facility based on a compact D-D Neutron generator," International Journal of Radiation Research, Oct. 2013, vol. 11, No. 4, p. 207.†
CICS Co., Ltd., "Development of Accelerator Type Neutron Capture Therapy System Using New Material Target Technology for Recurrent Cancer Therapy," Report of Research Products (Summery Version).†
Abstracts of meeting of Japan Society of Powder and Powder Metallurgy, Autumn Meeting 1998.†

\* cited by examiner
† cited by third party

Fig.6

[Table 1]

| | Neutron Flux(n / cm^2 / sec) | | | Gamma Dose (Gy / h) | Mix Rate | |
|---|---|---|---|---|---|---|
| | Fast | Epithermal | Thermal | | Fast Neutrons (Gy·cm^2) | Gamma-rays (Gy·cm^2) |
| MgF2 = 100wt% | 5.35E+08 | 4.41E+09 | 8.31E+07 | 0.48 | 6.30E-13 | 3.04E-14 |
| MgF2 : CaF2 = 98wt% : 2wt% | 5.51E+08 | 4.48E+09 | 8.89E+07 | 0.59 | 6.15E-13 | 3.67E-14 |
| MgF2 : CaF2 = 95wt% : 5wt% | 5.77E+08 | 4.41E+09 | 9.24E+07 | 0.55 | 6.43E-13 | 3.49E-14 |
| MgF2 : CaF2 = 92wt% : 8wt% | 5.85E+08 | 4.42E+09 | 8.62E+07 | 0.56 | 6.67E-13 | 3.51E-14 |
| MgF2 : CaF2 = 90wt% : 10wt% | 5.85E+08 | 4.43E+09 | 7.75E+07 | 0.45 | 6.68E-13 | 2.81E-14 |
| MgF2 : CaF2 = 80wt% : 20wt% | 6.39E+08 | 4.44E+09 | 7.97E+07 | 0.68 | 7.47E-13 | 4.25E-14 |
| MgF2 : CaF2 = 60wt% : 40wt% | 7.93E+08 | 4.66E+09 | 7.25E+07 | 0.80 | 8.46E-13 | 4.76E-14 |
| MgF2 : CaF2 = 40wt% : 60wt% | 1.03E+09 | 4.68E+09 | 9.98E+07 | 0.42 | 1.02E-12 | 2.47E-14 |
| MgF2 : CaF2 = 20wt% : 80wt% | 1.26E+09 | 4.63E+09 | 9.35E+07 | 0.55 | 1.20E-12 | 3.30E-14 |
| MgF2 : CaF2 = 10wt% : 90wt% | 1.43E+09 | 4.69E+09 | 8.27E+07 | 0.47 | 1.40E-12 | 2.81E-14 |
| CaF2 = 100wt% | 1.64E+09 | 4.74E+09 | 9.42E+07 | 0.66 | 1.59E-12 | 3.87E-14 |

Fig.7
[Table 2]

| | Raw Material, Molding | | | | Preliminary Sintering | | | Sintering [Primary, Secondary] | | Density of Sintered Body | | | Neutron Flux after Moderation (n/cm^2/sec) | | | Mix Rate of Fast Neutrons after Moderation (Gy·cm^-2) | Mechanical Strengths | | Overall Evaluation |
|---|---|---|---|---|---|---|---|---|---|---|---|---|---|---|---|---|---|---|---|
| | Mean Particle Diameter of Raw Material (μm) | Mix Proportion of CaF2 (wt%) | Added Sintering Aid (wt%) | Uniaxial Press Pressure (MPa) | CIP Molding Pressure (MPa) | Atmosphere | Heating Temperature (°C)×Holding Time(Hr) | Atmosphere | Heating Temperature(°C)×Holding Time(Hr) | Bulk Density (g/cm^3) | True Density (g/cm^3) | Relative Density (%) | Fast Neutrons | Epithermal Neutrons | Thermal Neutrons | | Bending Strength (MPa) | Vickers Hardness | |
| Example1 | 4 | 1.5 | CMC 0.1 | 20 | 20 | Air | 650×6 | N2 | 800×8, 1050×1.5 | 3.02 | 3.15 | 95.9 | 5.3E+08 | 4.4E+09 | 8.5E+07 | 6.6E-13 | 18 | 98 | ◎ |
| Example2 | 6 | 0.2 | CMC 0.1 | 20 | 20 | Air | 640×6 | He | 800×5, 920×1 | 2.97 | 3.15 | 94.3 | 5.6E+08 | 4.5E+09 | 9.0E+07 | 6.7E-13 | 15 | 90 | ◎ |
| Example3 | 4 | 2 | SAC 1.0 | 30 | 30 | Air | 700×6 | Air | 840×8, 1150×0.75 | 3.06 | 3.15 | 97.1 | 5.2E+08 | 4.3E+09 | 8.3E+07 | 6.1E-13 | 22 | 104 | ◎ |
| Example4 | 4 | 3 | CMC 0.03 | 30 | 30 | Air | 660×8 | N2 | 830×6, 1080×2 | 3.07 | 3.15 | 97.5 | 5.3E+08 | 4.3E+09 | 8.3E+07 | 6.0E-13 | 27 | 108 | ◎ |
| Example5 | 4 | 7.5 | SAC 0.07 | 40 | 40 | Air | 690×8 | N2 | 830×9, 1080×2 | 3.06 | 3.15 | 97.1 | 5.8E+08 | 4.4E+09 | 8.5E+07 | 6.3E-13 | 25 | 110 | ◎ |
| Example6 | 5 | 18 | CMC 0.3 | 6 | 15 | Air | 630×8 | N2 | 820×6, 930×4 | 2.98 | 3.15 | 94.6 | 6.2E+08 | 4.5E+09 | 7.8E+07 | 7.7E-13 | 21 | 108 | ○ |
| Example7 | 5 | 25 | CMC 0.1 | 30 | 30 | Air | 650×6 | N2 | 840×5, 1150×0.5 | 3.01 | 3.15 | 95.6 | 6.0E+08 | 4.5E+09 | 7.5E+07 | 7.5E-13 | 28 | 113 | ○ |
| Example8 | 4 | 50 | CMC 1.0 | 7 | 12 | Air | 600×5 | N2 | 860×8, 1080×2 | 3.02 | 3.16 | 95.6 | 7.5E+08 | 4.6E+09 | 8.8E+07 | 8.6E-13 | 35 | 130 | ○ |
| Example9 | 6 | 50 | CMC 1.0 | 30 | 30 | Air | 610×7 | N2 | 860×8, 970×4 | 3.00 | 3.16 | 94.9 | 9.2E+08 | 4.7E+09 | 9.2E+07 | 1.0E-12 | 30 | 122 | ○ |
| Example10 | 4 | 75 | SAC 0.07 | 8 | 10 | Air | 650×5 | N2 | 880×8, 1060×3 | 3.02 | 3.17 | 95.3 | 1.2E+09 | 4.7E+09 | 9.2E+07 | 1.1E-12 | 38 | 142 | ○ |
| Example11 | 5 | 88 | CMC 1.0 | 30 | 30 | Air | 650×5 | N2 | 880×8, 950×4 | 3.01 | 3.17 | 95.0 | 1.3E+09 | 4.7E+09 | 8.9E+07 | 1.2E-12 | 36 | 140 | ○ |
| Example12 | 4 | 88 | CMC 1.0 | 8 | 10 | Air | 650×5 | He | 880×8, 1120×2 | 3.04 | 3.17 | 95.9 | 1.4E+09 | 4.7E+09 | 8.7E+07 | 1.1E-12 | 45 | 150 | ○ |
| Comparative Example1 | 8 | 1.5 | SAC 0.07 | 20 | 20 | Air | 550×8 | N2 | 670×6, 1200×2 | 2.93 | 3.15 | 93.0 | 1.9E+09 | 4.5E+09 | 8.6E+07 | 1.8E-12 | 10 | 56 | △ |
| Comparative Example2 | 10 | 0.2 | CMC 0.1 | 4 | 4 | Air | 600×6 | N2 | 830×5, 950×4 | 2.90 | 3.15 | 92.1 | 2.1E+09 | 4.6E+09 | 8.5E+07 | 2.0E-12 | 8 | - | × |
| Comparative Example3 | 12 | 5 | CMC 1.0 | 20 | 20 | Air | 700×10 | N2 | 900×10, 1200×4 | - | 3.15 | - | 2.4E+09 | 4.7E+09 | 8.8E+07 | 2.4E-12 | - | - | × |
| Comparative Example4 | 8 | 5 | CMC 0.1 | 3 | 3 | Air | 600×6 | N2 | 900×5, 1200×2 | 2.92 | 3.15 | 92.7 | 2.2E+09 | 4.6E+09 | 8.2E+07 | 2.0E-12 | 10 | 62 | × |
| Comparative Example5 | 8 | 25 | CMC 0.1 | 30 | 30 | Air | 550×8 | N2 | 870×6, 1160×3 | 2.93 | 3.15 | 93.0 | 2.3E+09 | 4.7E+09 | 8.0E+08 | 2.3E-12 | 12 | 80 | × |
| Comparative Example6 | 8 | 25 | CMC 0.1 | 4 | 4 | Air | 600×6 | N2 | 830×5, 950×4 | 2.91 | 3.15 | 92.4 | 2.4E+09 | 4.7E+09 | 8.7E-08 | 2.5E-12 | 14 | 100 | × |
| Comparative Example7 | 8 | 50 | CMC 0.1 | 20 | 20 | Air | 550×8 | N2 | 880×5, 1200×2 | 2.91 | 3.16 | 92.1 | 2.5E+09 | 4.7E+09 | 9.3E+08 | 2.7E-12 | 15 | 98 | × |
| Comparative Example8 | 8 | 50 | CMC 0.1 | 4 | 4 | Air | 600×6 | N2 | 850×5, 960×4 | 2.92 | 3.16 | 92.4 | 2.4E+09 | 4.7E+09 | 8.7E+08 | 2.6E-12 | 15 | 102 | × |
| Comparative Example9 | 8 | 50 | CMC 0.1 | 20 | 20 | Air | 530×8 | N2 | 900×6, 1160×4 | 2.90 | 3.17 | 91.5 | 3.2E+09 | 4.9E+09 | 1.2E+09 | 3.0E-12 | 18 | 108 | × |
| Comparative Example10 | 8 | 88 | CMC 0.1 | 4 | 4 | Air | 600×6 | N2 | 860×6, 970×5 | 2.93 | 3.17 | 92.4 | 3.0E+09 | 4.8E+09 | 1.0E+09 | 2.9E-12 | 25 | 114 | × |
| Comparative Example11 | 8 | 88 | CMC 0.03 | 30 | 30 | Air | 660×8 | N2 | 1060×2 | 2.93 | 3.15 | 93.0 | 2.3E+09 | 4.6E+09 | 8.2E+07 | 2.4E-12 | 13 | 75 | × |
| Comparative Example12 | 8 | 3 | CMC 0.03 | 30 | 30 | Air | 650×6 | N2 | 1150×1.5 | 2.90 | 3.15 | 92.1 | 2.6E+09 | 4.7E+09 | 9.3E+07 | 2.8E-12 | 12 | 62 | × |
| Comparative Material(MgF2) | 5 | 0 | CMC 0.1 | 20 | 20 | Air | 600×6 | N2 | 840×6, 1100×2 | 2.97 | 3.15 | 94.3 | 5.4E+08 | 4.4E+09 | 9.0E+08 | 8.0E-13 | 16 | 90 | ○ |
| Comparative Material(CaF2) | 5 | 100 | CMC 0.1 | 20 | 20 | Air | 600×6 | N2 | 880×6, 1130×2 | 3.00 | 3.18 | 94.3 | 1.7E+09 | 4.7E+09 | 9.5E+08 | 2.0E-12 | 40 | 145 | × |

Note 1) "-" means unmeasurable.

$MgF_2$—$CaF_2$ BINARY SYSTEM SINTERED BODY FOR RADIATION MODERATOR AND METHOD FOR PRODUCING THE SAME

TECHNICAL FIELD

The present invention relates to a $MgF_2$—$CaF_2$ binary system sintered body for a radiation moderator and a method for producing the same, and more particularly, to a $MgF_2$—$CaF_2$ binary system sintered body for a radiation moderator having a compact structure suitable for a moderator to restrict the radiation velocity and energy of radioactive rays of every kind such as neutrons and a method for producing the same.

BACKGROUND ART

Among fluorides, a calcium fluoride ($CaF_2$) single crystal body, a magnesium fluoride ($MgF_2$) single crystal body and the like have been used in the optical field, for example, in the vacuum ultraviolet region of wavelengths of 160 nm or less, or in the extreme infrared region of wavelengths of 3 μm or more. They have been used as a lens, a prism and the like for such specific wavelength regions wherein light does not pass through the glass members widely used in the market such as a very-high-purity quart glass and optical glasses. Therefore, they are naturally expensive optical members.

Generally speaking, there are very few cases where a fluoride is used for other than such optical uses. The $CaF_2$ single crystal body, a lithium fluoride (LiF) single crystal body, or an aluminum fluoride ($AlF_3$) single crystal body has been rarely used as a shield to neutrons, one of radioactive rays. However, such single crystal bodies have plane orientation dependency of moderation performance originated in crystal orientation and ununiformity due to structural defects such as subgrains, and moreover, they are extremely expensive.

The radioactive rays are roughly classified into alpha ($\alpha$)-rays, beta ($\beta$)-rays, gamma ($\gamma$)-rays, X-rays, and neutrons. The power passing through a substance (penetrability) gradually increases in this order.

The neutrons which have the highest penetrability among them are further classified into the below-described groups, for example, according to the energy level which they have. The energy each type of neutrons has is shown in parentheses, and the larger the value is, the higher the penetrability is.

In the order of the lowest penetrability, they are classified into cold neutrons (up to 0.002 eV), thermal neutrons (up to 0.025 eV), epithermal neutrons (up to 1 eV), slow neutrons (0.03-100 eV), intermediate neutrons (0.1-500 keV) and fast neutrons (500 keV or more).

Here, there are various views concerning the classification of neutrons, and the energy values in the parentheses are not precise. For example, there is a view that mentions 40 KeV or less, which is within the above energy region of intermediate neutrons, as the energy of epithermal neutrons.

The typical effective utilization of neutrons is an application to the medical care field. In particular, the radiation therapy in which tumor cells such as malignant cancers are irradiated with neutrons so as to be broken has been coming into general use in recent years.

In order to obtain medical effects in the present radiation therapy, neutrons of a certain high energy must be used, so that in the irradiation of neutrons, the influence on a healthy part other than an affected part of a patient cannot be avoided, leading to side effects. Therefore, in the present situation, the application of the radiation therapy is limited to severe patients.

When a normal cell is exposed to high-energy neutrons, its DNA is damaged, leading to side effects such as dermatitis, anemia due to radiation and leukopenia. Furthermore, in some cases, a late injury may be caused some time after treatment, and a tumor may be formed and bleed in the rectum or the urinary bladder.

In recent years, in order not to cause such side effects and late injuries, methods of pinpoint irradiation on a tumor have been studied. Examples thereof are: "Intensity Modulated Radiation Therapy (IMRT)" in which a tumor portion is three-dimensionally irradiated accurately with a high radiation dose; "Motion Tracking Radiation Therapy" in which radiation is emitted to motions in the body of a patient such as breathing or heartbeat; and "Particle Beam Radiation Therapy" in which a baryon beam or a proton beam each having a high remedial value is intensively emitted.

The half-life of a neutron is short, about 15 min. The neutron decays in a short period of time, releases electrons and neutrinos, and turns into protons. And the neutron has no charge, and therefore, it is easily absorbed when it collides with a nucleus. The absorption of neutrons in such a manner is called neutron capture, and one example of an application of neutrons to the medical care field by use of this feature is the below-described "Boron Neutron Capture Therapy (hereinafter, referred to as BNCT)", a new cancer therapy which is recently gaining attention.

In this BNCT, by causing tumor cells such as malignant cancers to react with a boron drug which is injected into the body by an injection, a reaction product of a boron compound is formed in the tumor portion.

The reaction product is then irradiated with neutrons of an energy level which has less influences on a healthy part of the body (desirably comprising mainly epithermal neutrons, and low-energy-level neutrons being lower than epithermal neutrons). And a nuclear reaction with the boron compound is caused only within a very small range, resulting in making only the tumor cells extinct.

Originally, cancer cells easily take boron into them in the process of vigorously increasing, and in the BNCT, by use of this feature, only the tumor portion is effectively broken.

This method was proposed about 60 years ago. Because of small influences on a healthy part of a patient, it has been attracting attention as an excellent radiation therapy since quite long before and has been researched and developed in varied countries.

However, there are wide-ranging important problems on the development such as development of a neutron generator and a device for a selection of the types of neutrons to be remedially effective, and avoidance of influences on a healthy part other than an affected part of a patient (that is, formation of a boron compound only in a tumor portion). Therefore, the method has not come into wide use as a general therapy. Significant factors in terms of apparatus why it has not come into wide use are insufficient downsizing of the apparatus and insufficient enhancement of its performance.

For example, there is a latest system of the BNCT, which a group with Kyoto University as the central figure has been promoting (Non-Patent Document 1 and Non-Patent Document 2). This system comprises an apparatus for medical use only, having a cyclotron accelerator as a neutron generator which is exclusively installed without being attached to an existing nuclear reactor.

One report says that the accelerator alone weighs about 60 tons, and its size is quite large. In the cyclotron system, protons are accelerated by use of a centrifugal force in a circular portion of the cyclotron and caused to collide with a target metal such as a plate made of beryllium (Be) so as to generate fast neutrons. In order to efficiently generate neutrons, it is required to make the diameter of the circular portion large so as to obtain a large centrifugal force. That is one of the reasons why the apparatus is large.

Furthermore, in order to safely and effectively utilize the generated radiation (mainly neutrons), a radiation shield such as a shielding plate (hereinafter, referred to as a moderator) is required. As moderators, polyethylene containing $CaF_2$ or LiF, as well as Pb, Fe, Al and polyethylene, are selected. It cannot be said that the moderation performance of these moderators is sufficient, and in order to conduct required moderation, the moderator becomes quite thick. Therefore, the moderation system device portion including the moderator is also one of the reasons why the apparatus is large.

In order to allow this BNCT to come into wide use in general hospitals, hereinafter, downsizing of the apparatus is necessary. In addition to further downsizing of the accelerator, to improve the remedial values by developing a moderator having high moderation performance and achieve downsizing of the moderation system device by the improvement of moderation performance is an urgent necessity. The moderator which is important for downsizing a BNCT apparatus and improving remedial values is described below.

As described above, in order to safely and effectively utilize radiation, it is necessary to arrange a moderator having the right performance in the right place. In order to effectively utilize neutrons having the highest penetrability among radioactive rays, it is important to accurately know the moderation performance of every kind of substances to neutrons so as to conduct effective moderation.

One example of the selection of particle beam types in order to effectively utilize neutrons for medical care is shown below.

By removing high-energy neutrons which adversely influence the body (such as fast neutrons and a high-energy part of intermediate neutrons) as much as possible, and by further reducing extremely-low-energy neutrons having little medical effect (such as thermal neutrons and cold neutrons), the ratio of neutrons having high medical effects (such as a low-energy part of intermediate neutrons and epithermal neutrons) is increased.

As a result, a particle beam effectively utilized for medical treatment can be obtained. The low-energy part of intermediate neutrons and epithermal neutrons have a relatively high invasive depth to the internal tissues of a patient. Therefore, for example, in the case of irradiating the head with the low-energy part of intermediate neutrons and epithermal neutrons, without craniotomy required, as far as the tumor is not present in a considerably deep part, it is possible to carry out effective irradiation to an affected part in an unopened state of the head.

On the other hand, when the extremely-low-energy neutrons such as thermal neutrons are used in an operation, because of their low invasive depth, craniotomy is required, resulting in a significant burden on the patient.

In order to improve remedial values in the BNCT, it is required to irradiate an affected part with a large quantity of neutrons comprising mainly epithermal neutrons and some thermal neutrons.

Specifically, an estimated dose of epithermal neutrons and thermal neutrons required in cases where the irradiation time is in the order of one hour, is about $1 \times 10^9$ [n/cm²/sec]. In order to secure the dose, it is said that as the energy of an outgoing beam from an accelerator being a source of neutrons, about 5 MeV-10 MeV is required when beryllium (Be) is used as a target for the formation of neutrons.

The selection of particle beam types through moderators of every kind in a neutron radiation field for BNCT using an accelerator is described below.

A beam emitted from the accelerator collides with a target (Be, in this case), and by nuclear reaction, high-energy neutrons (fast neutrons) are mainly generated. As a method for moderating the fast neutrons, using lead (Pb) and iron (Fe) each having a large inelastic scattering cross section, the neutrons are moderated to some extent. In order to further moderate the neutrons moderated to some extent (approximately, up to 1 MeV), optimization of the moderator according to the neutron energy required in the radiation field is required.

As a moderator, aluminum oxide ($Al_2O_3$), aluminum fluoride ($AlF_3$), calcium fluoride ($CaF_2$), graphite, heavy water ($D_2O$) or the like is generally used. By injecting the neutrons moderated nearly to 1 MeV into these moderators, they are moderated to the epithermal neutron region of the energy suitable for BNCT (4 keV-40 keV).

In the case of the above Non-Patent Document 1 and Non-Patent Document 2, as moderators, Pb, Fe, polyethylene, Al, $CaF_2$ and polyethylene containing LiF are used. The polyethylene and polyethylene containing LiF among them are used as moderators for safety (mainly for shielding) which cover the outside portion of the apparatus in order to prevent leakage of high-energy neutrons out of the radiation field.

It can be said that it is appropriate to moderate the high-energy part of neutrons to some extent using Pb and Fe among these moderators (the first half of the stage of moderation), but it cannot be said that the second half of the stage of moderation using Al and $CaF_2$ after the moderation to some extent is appropriate.

That is because the moderators used in the second half of the stage thereof has insufficient shielding performance to fast neutrons, and a high ratio of fast neutrons having a possibility of bad influences on healthy tissues of a patient is left in the moderated neutron type.

By reason of $CaF_2$ having insufficient shielding performance to the high-energy part of neutrons as a moderator used in the second half of the stage thereof, part of them passes without being shielded.

The polyethylene containing LiF used with $CaF_2$ in the second half of the stage thereof covers over the entire surface except an outlet of neutrons on the treatment room side. It is arranged so as to prevent whole-body exposure of a patient to the fast neutrons, without having a function as a moderator on the outlet of neutrons.

For information, the polyethylene among the moderators in the first half of the stage thereof covers over the entire surface of the periphery of the apparatus except the treatment room side, like the polyethylene containing LiF in the second half of the stage thereof, and it is arranged so as to prevent the fast neutrons from leaking to the surroundings of the apparatus.

Therefore, instead of $CaF_2$ as a shielding member to fast neutrons in the second half of the stage thereof, the development of a moderator which can shield and moderate high-energy neutrons while suppressing the attenuation of intermediate-level-energy neutrons required for treatment has been desired.

From various kinds of researches/studies, the present inventors found a $MgF_2$ sintered body or $MgF_2$ system substances, more specifically, a $MgF_2$—$CaF_2$ binary system sintered body as a moderator which makes it possible to obtain neutrons (neutrons of the energy of 4 keV-40 keV) mainly comprising epithermal neutrons in anticipation of the highest remedial value, from the above neutrons moderated to some extent (the energy thereof is approximately up to 1 MeV). As the $MgF_2$ system substances, a $MgF_2$—LiF binary system sintered body, a $MgF^2$—$CaF_2$—LiF ternary system sintered body other than the $MgF_2$—$CaF_2$ binary system sintered body can be exemplified.

As of now, there has been no report that magnesium fluoride ($MgF_2$) was used as a moderator to neutrons, not to mention that there has been no report that a $MgF_2$ sintered body or a $MgF_2$—$CaF_2$ binary system sintered body was used as such neutron moderator.

The present inventors has filed an application of an invention relating to a sintered body of $MgF_2$ simple (a technical term related to raw material technology, a synonym for "single") prior to this invention (Patent Document 1: Japanese Patent Application No. 2013-142704, hereinafter, referred to as the prior application).

$MgF_2$ is a colorless crystal, having a melting point of 1248° C., a boiling point of 2260° C., a density (i.e. true density) of 3.15 g/cm$^3$, a cubic system and a rutile structure according to a science and chemistry dictionary. On the other hand, $CaF_2$ is a colorless crystal, having a melting point of 1418° C., a boiling point of 2500° C., a density (i.e. true density) of 3.18 g/cm$^3$, a Moh's hardness of 4, a cubic system and a fluorite structure.

A single crystal body of $MgF_2$ has high transparency, and since high light transmittance is obtained within a wide range of wavelengths of 0.2 μm-7 μm and it has a wide band gap and high laser resistance, it has been mainly used as a window material for eximer laser. Or when a $MgF_2$ single crystal body is deposited on the surface of a lens, it shows effects of protection of the inner parts thereof or prevention of irregular reflection. In either case, it is used for optical use.

On the other hand, since the $MgF_2$ sintered body has low transparency because of its polycrystalline structure, it is never used for optical use. Since the $MgF_2$ sintered body has high resistance to fluorine gas and inert gas plasma, a few patent applications concerning an application thereof to a plasma-resistant member in the semiconductor producing process have been filed. However, there is no publication or report that it was actually used in the semiconductor producing process. That is because the $MgF_2$ single crystal body has a strong image of extremely high price and the $MgF_2$ sintered body produced by a general method has low mechanical strength as described in the below-mentioned Patent Document 2.

As for a $MgF_2$ sintered body, according to the Japanese Patent Application Laid-Open Publication No. 2000-302553 (the below-mentioned Patent Document 2), the greatest defect of ceramic sintered bodies of fluoride such as $MgF_2$, $CaF_2$, $YF_3$ and LiF is low mechanical strength. And in order to solve this problem, the invention was achieved, wherein a sintered body compounded by mixing these fluorides with alumina ($Al_2O_3$) at a predetermined ratio can keep excellent corrosion resistance of the fluorides as well as obtain high mechanical strength.

However, as for the corrosion resistance and mechanical strength of the sintered bodies produced by this method, in any combination, the sintered bodies are simply allowed to have just an intermediate characteristic between the characteristic of any of the fluorides and that of alumina. No sintered body having a characteristic exceeding one's characteristic superior to the other's has been obtained by compounding. In addition, their use is limited to high corrosion resistance uses, greatly different from the uses of the present invention.

Another sintered body mainly comprising $MgF_2$ is described in Japanese Patent Application Laid-Open Publication No. 2000-86344 (the below-mentioned Patent Document 3), but its use is also limited to a plasma-resistant member. In the Patent Document 3, a sintered body comprises a fluoride of at least one kind of alkaline earth metals selected from the group of Mg, Ca, Sr and Ba, in which the total amount of metallic elements other than the alkaline earth metals is 100 ppm or less on a metal basis, the mean particle diameter of crystal grains of the fluoride is 30 μm or less, and the relative density is 95% or more.

However, the materials in the list (Table 1) of Examples of the Patent Document 3 were obtained by firing a fluoride of each single kind of the above four alkaline earth metals (i.e. $MgF_2$, $CaF_2$, $SrF_2$ and $BaF_2$), and no fired mixture of those fluorides is described.

Still another example of an application of a sintered body mainly comprising $MgF_2$ to a plasma-resistant member is the Japanese Patent Application Laid-Open Publication No. 2012-206913 (the below-mentioned Patent Document 4). The Patent Document 4 discloses an invention wherein, since a sintered body of $MgF_2$ simple has a defect of low mechanical strength, by mixing at least one kind of non-alkaline metallic dispersed particles having a lower mean linear thermal expansion coefficient than $MgF_2$ such as $Al_2O_3$, AlN, SiC or MgO, the defect of low mechanical strength thereof can be compensated for.

However, when a sintered body of such mixture is used as the above moderator to neutrons, the moderation performance thereof is greatly different from that of $MgF_2$ simple because of the influence of the non-alkaline metal mixed into $MgF_2$. Therefore, it is easily predicted that it is difficult to apply a sintered body of this kind of mixture to a use as a moderator.

In addition, an example of an application of a sintered body mainly comprising $CaF_2$ to a plasma-resistant member is the Japanese Patent Application Laid-Open Publication No. 2004-83362 (the below-mentioned Patent Document 5). The Patent Document 5 describes a method wherein using hydrofluoric acid, impurities other than Mg is removed from a low-purity raw material containing Mg, so as to precipitate high-purity $CaF_2$, and a fluoride sintered body whose starting raw material is the high-purity $CaF_2$ containing Mg of 50 ppm or more and 5% by weight or less is produced. A problem here is a state of Mg contained in the starting raw material, though the state is not described at all. And there is no description concerning the technique by which the degree of purity of the low-purity raw material is raised using hydrofluoric acid.

Then, when presuming the process of raising the degree of purity of a low-purity raw material as a person skilled in the art, generally speaking, in the case of raising the degree of purity of a low-purity raw material using hydrofluoric acid, a method is often adopted, wherein impurities in the raw material are first dissolved into a hydrofluoric acid solution as many as possible, and if a component (Ca, here) desired to be a main raw material dissolved with impurities in this dissolution process, the component is precipitated and separated by use of the difference in solubility among the dissolved components.

When further reviewing the invention, it is presumed that Mg exhibited different dissolution behavior from other impurities. In the specification, it is referred to as only "Mg", and according to the descriptions of Examples in Table 1, as for high concentrations of impurity components other than Mg (such as Fe, Al, Na and Y), all of their concentrations were decreased by purity raising treatment, but only the concentration of Mg did not change, being 2000 ppm before the treatment and being also 2000 ppm after the treatment.

Hence, there is a high possibility that Mg might be in a state which is hard to dissolve in hydrofluoric acid, that is, a metal state. If $CaF_2$ containing metal Mg is a starting raw material, the sintering process thereof is very different from the case like the present invention wherein a mixture of $CaF_2$ and $MgF_2$ is a starting raw material, and the characteristics of the sintered bodies are also very different from each other.

On the other hand, an invention relating to a neutron moderator was disclosed lately. That is the Japanese Patent No. 5112105 (Patent Document 6). The Patent Document 6 discloses 'a moderator which moderates neutrons, comprising a first moderating layer obtained by melting a raw material containing calcium fluoride ($CaF_2$), and a second moderating layer comprising metal aluminum (Al) or aluminum fluoride ($AlF_3$), the first moderating layer and the second moderating layer being adjacent to each other'.

In the Patent Document 6, the first moderating layer obtained by melting the raw material containing $CaF_2$ is disclosed, but raw material conditions such as the purity, components, particle size and treatment method thereof, and melting conditions such as heating temperatures, holding times thereof and the type of heating furnace are not mentioned at all, very insincerely described as a patent specification. In the Patent Document 6, there is no description suggesting that something related to $MgF_2$ should be used as a neutron moderator.

In the preceding documents, as described above, there is no description suggesting the use of a sintered body of $MgF_2$ as a moderator to neutrons, one kind of radiation. In such situation, the present inventors found that it was possible to use a $MgF_2$ sintered body with a modification made thereto as a moderator to neutrons, one kind of radiation, and achieved the invention of the prior application.

In the invention of the prior application, a high-purity $MgF_2$ raw material is pulverized and two-stage compressing and molding step is conducted thereon. That is, after molding by a uniaxial press molding method, this press molded body is further molded by a cold isostatic pressing (CIP) method so as to form a CIP molded body.

Then, by firing the same with three-level heating conditions using an atmosphere-adjustable normal pressure furnace, a sintered body having a compact structure is produced with suppressing foaming of $MgF_2$ as much as possible.

However, since $MgF_2$ very easily generates foams, it is not easy to actually suppress its foaming. As a result, the range of relative densities (i.e. 100×[bulk density of a sintered body]/[true density](%)) of sintered bodies produced by this method was 92%-96%, and the mean value thereof was of the order of 94%-95%.

A characteristic desired for a sintered body for a neutron moderator is 'the mean value of relative densities of 95% or more at least, desirably 96% or more should be stably secured'.

In order to achieve the characteristic, the present inventors worked toward further development and found that when using a $MgF_2$—$CaF_2$ binary system sintered body for radiation use, the relative density thereof could be easily improved, compared with a sintered body of $MgF_2$ simple, and that by making the sintering conditions proper, sintered bodies having more desirable densities could be stably produced, leading to the completion of the present invention.

PRIOR ART DOCUMENT

Patent Document

Patent Document 1: Japanese Patent Application No. 2013-142704 (filed on Jul. 8, 2013)
Patent Document 2: Japanese Patent Application Laid-Open Publication No. 2000-302553
Patent Document 3: Japanese Patent Application Laid-Open Publication No. 2000-86344
Patent Document 4: Japanese Patent Application Laid-Open Publication No. 2012-206913
Patent Document 5: Japanese Patent Application Laid-Open Publication No. 2004-83362
Patent Document 6: Japanese Patent No. 5112105

Non-Patent Document

Non-Patent Document 1: H. Tanaka et al., Applied Radiation and Isotopes 69 (2011) 1642-1645
Non-Patent Document 2: H. Tanaka et al., Applied Radiation and Isotopes 69 (2011) 1646-1648
Non-Patent Document 3: Hiroaki Kumada, Tetsuya Yamamoto, Dose Evaluation of Neutron Capture Therapy in JRR-4, Health Physics, 42(1), (2007) 23-37

SUMMARY OF THE INVENTION

Solution to Problem and Advantageous Effect of Invention

The present invention was developed in order to solve the above problems, and it is an object of the present invention to provide a $MgF_2$—$CaF_2$ binary system sintered body for a radiation moderator, having excellent characteristics as a moderator used for moderating the energy of neutrons, a kind of radiation, in the good use of the neutrons for therapy, which makes it possible to enhance remedial values and downsize an apparatus for therapy, and which is inexpensive unlike a single crystal body, and a method for producing the same.

It is another object of the present invention to provide a $MgF_2$—$CaF_2$ binary system sintered body for a radiation moderator having a very compact structure, without plane orientation dependency of the moderation performance originated in crystal orientation, unlike a single crystal body having such plane orientation dependency, and without ununiformity based on the structural defects such as sub-grains, and a producing method by which such sintered bodies can be stably produced.

The present inventors first gave basic consideration to the selection of substances (compounds) suitable for a moderator which performs shielding (i.e. moderation) to high-energy neutrons.

That is, they first conducted relative research on the moderation performance to neutrons of substances of each kind.

Here, whether or not neutrons moderated to intermediate energy in the wide energy range of neutrons can be moderated to an energy level with which a patient can be irradiated, was examined.

As compounds to be examined, since the energy level of the injected neutrons was intermediate, compounds containing halogen elements, being compounds of relatively light elements were considered. Fluorides such as calcium fluoride ($CaF_2$) and magnesium fluoride ($MgF_2$), or chlorides such as calcium chloride ($CaCl_2$) and magnesium chloride ($MgCl_2$) were first conceived.

Since chlorides easily generate molten salt (a liquid phase) at heating in producing the processed articles thereof, sintering reaction caused by use of the formation of a solid solution in which a solid phase and a liquid phase are mixed, is difficult to be caused therein. Even if a sintered body can be generated, it becomes chemically active and there is a high risk of lack of stability.

Compared with chlorides, sintered bodies of fluorides are relatively chemically stable, and therefore, fluorides were selected in anticipation of superiority thereof over chlorides.

As the basic characteristics required for a moderator other than moderation performance, a characteristic of keeping the shape of the product is exemplified. It is important to be excellent in mechanical strength with which damage in mechanical processing and in handling during manufacturing the product can be prevented.

The mechanical strength of a sintered body is determined by micro strength of bonding parts between particles, the compactness of the sintered body, and moreover, the brittleness originated from a crystal structure (such as polycrystal or single crystal or amorphous) of the parent thereof.

The compactness of the sintered body is determined by the defoaming state such as the sizes, shapes, distribution and number of bubbles, in other words, the shape such as the width and length of the bonding parts and a bound body (parent) of ex-particles.

Basic technical ideas of the present invention are:

(1) relaxing the sintering conditions by mixing two kinds of raw materials, that is, making it possible to conduct sintering at a lower temperature than the case of a raw material of one kind simple;

(2) by regulating the particle size of the raw material provided to the sintering reaction, the particle growth by solid phase reaction is promoted, and a compact sintered body having strong cohesion between particles through the formation of a solid solution is formed; and (3) when a raw material of fluoride is heated at a high temperature, part of the raw material vaporizes (mainly part of the fluoride is thermally decomposed (sublimates) and generates fluorine gas), leading to the formation of bubbles (foaming). By sintering at a temperature low enough to avoid this foaming and making the process of heating (sintering heat pattern) proper, a compact sintered body is produced.

By combining all the above technical ideas (1), (2) and (3), the present invention aims to stably produce fluoride sintered bodies of $MgF_2$—$CaF_2$ binary system for a radiation moderator excellent in moderation performance required as a member for a moderator to radiation, especially to neutrons and mechanical strength (shape keeping) characteristic as a fundamental characteristic other than the moderation performance.

In the present invention, the $MgF_2$—$CaF_2$ binary system sintered body is mentioned mainly as a moderator to neutrons, but the sintered body has excellent performance as a member for shielding to not only neutrons but also other radioactive rays such as X-rays or gamma-rays.

Concerning the technical idea (1), as shown in FIG. 4, each of the $MgF_2$—$CaF_2$ binary system sintered bodies within a range of good sintering conditions has a relative density, for example, the highest attained relative density tending to be higher by the order of 0.5%-1.5% than the sintered bodies of $MgF_2$ simple. And the temperature limits of the secondary sintering temperature of the $MgF_2$—$CaF_2$ binary system sintered bodies, in which the bulk densities thereof become high, are wider, and it means that the stable sintering conditions can be easily satisfied.

Concerning the technical idea (2), the effect of the particle size control of the raw material is described below.

The chief object thereof is to make the particle size condition of the raw material proper so as to promote sintering by firing at a low temperature (hereinafter, referred to as 'low-temperature sintering').

As the conditions of the raw material, each of high-purity raw material powders for a starting raw material (the mean particle diameter of the raw material powders was about 140 µm in median diameter) was pulverized by the below-mentioned pulverization method, and provided to the subsequent treatment step, and the characteristic evaluation of the completed sintered body was conducted. As a result, it was found that:

(i) the particle size distribution range should be small, specifically, the maximum particle diameter should be 50 µm or less, desirably 30 µm or less;

(ii) as a preferable state of the particle size distribution, the shape of the particle size distribution curve drawn with particle diameter (unit: µm) as the abscissa and particle diameter ratio (ratio of every particle diameter, unit: wt. %) as the ordinate, should be not '2-peak type' or '3-peak type', but '1-peak type' or 'sub-1-peak type', when the shapes of the particle size distribution curves are divided into '1-peak type', 'sub-1-peak type', '2-peak type' and '3-peak type' as the shapes of mountain ranges are expressed;

(iii) the mean particle diameter should be 6 µm or less, desirably 4 µm or less in median diameter; and by simultaneously satisfying these conditions of the items (i), (ii) and (iii), the sintered body could be allowed to have a high density, leading to a noticeable improvement of moderation performance as a neutron moderator.

The foaming phenomenon in the above technical idea (3) is described below. Using a differential thermal analyzer, alterations in weight and in endothermic and exothermic amount of the sample of the starting raw material were examined while heating. As a result, a minute quantity of weight decrease was found at approximately 800° C.-850° C., though there were slight differences depending on the mix proportion of the starting raw material. It appears that fluorine attached to a parent of a preliminary sintered body or fluorine resolving in the parent, for example, with a weak bonding property, dissociated and decomposed first of all. After further heating, a point of inflection of the weight decrease curve appeared at approximately 850° C.-900° C., and the weight decrease became noticeable.

The results of this differential thermal analysis, and the examination results of the sintering conditions and the structure of the sintered body in a preliminary sintering test below-mentioned, specifically, the examination results such as 1. the situation of bubble generation in the sintered body, 2. the situation of tissue structure of the sintered portion, and 3. the bulk density of the sintered body were totally considered. It was anticipated that when heated at a temperature of the point of inflection of the weight decrease curve or higher, part of bonded fluorine element in $MgF_2$ or $CaF_2$ would start to decompose, and cause the generation of fluorine gas, leading to the formation of fine bubbles.

Then, the temperature of this point of inflection, 850° C.-900° C. is referred to as the starting temperature of foaming (Tn). The temperature at which vaporization started was slightly different depending on the composition. In the case of a composition mainly comprising $MgF_2$ ($MgF_2$ of 70-99.8% by weight, and $CaF_2$ of the rest), vaporization started at about 800° C. and it became quite brisk at about 850° C. (the point of inflection, that is, the starting temperature of foaming Tn was decided to be 850° C.). In the case of a composition mainly comprising $CaF_2$ ($MgF_2$ of 10-40% by weight, and $CaF_2$ of the rest), vaporization started at about 850° C. and it became quite brisk at about 900° C. (similarly, Tn was decided to be 900° C.). In the case of $MgF_2$ of 40-70% by weight and $CaF_2$ of the rest, vaporization started at around the intermediate temperature between the above two cases, that is, in the temperature limits of about 825° C. or more, and it became quite brisk at about 875° C. (similarly, Tn was decided to be 875° C.).

That is, in the case of the composition mainly comprising $MgF_2$ ($MgF_2$ of 70-99.8% by weight, and $CaF_2$ of the rest), sublimation starts at about 800° C., and it becomes brisk and foaming starts at about 850° C. In the case of the composition mainly comprising $CaF_2$ ($MgF_2$ of 10-40% by weight, and $CaF_2$ of the rest), sublimation starts at about 850° C. and it becomes brisk and foaming starts at about 900° C. In the case of $MgF_2$ of 40-70% by weight, and $CaF_2$ of the rest, the mix proportion intermediate therebetween, sublimation starts at about 825° C., and it becomes brisk and foaming starts at about 875° C.

Thus, when a fluoride sublimates (a phenomenon in which a solid phase changes into a gas phase without passing through a liquid phase. In this case, a synonym for "vaporize"), fluorine gas is generated, resulting in generation of fine bubbles in the sintered body.

The shapes of the generated bubbles are almost spheres. When observing the broken-cross section of the sintered body with an electron microscope (SEM), the cross sections of bubbles look like circles close to true circles. The sizes of the bubbles range from small ones of several μm to large ones of 20 μm-40 μm in diameter seen on the broken-cross section.

The shapes of the small ones of several μm are approximately circles and the shapes of the large ones are rarely circles. Most of them are irregular such as long and narrow, or angular. Judging from these shapes, it is considered that the small ones are bubbles which have just been generated, and that the large ones are aggregates of some of the generated bubbles or residuals originated from voids between particles or the like which could not defoam in the sintering process.

The reason why the value of relative density is shown by range corresponding to one value of bulk density is because in the case of a binary system sintered body of $MgF_2$ and $CaF_2$, the true densities of the both are different (that of $MgF_2$ is 3.15 $g/cm^3$, while that of $CaF_2$ is 3.18 $g/cm^3$), and therefore, depending on the mix proportion thereof, the true density of the mixture varies slightly. Here, the value of true density of the mixture is decided as shown below, so as to calculate the relative density thereof.

It is decided that:

(1) the true density is 3.15 $g/cm^3$, in the case of a composition mainly comprising $MgF_2$, that is, $MgF_2$ of 70% by weight or more and 99.8% by weight or less (referred to as 70-99.8% by weight in the present application) and $CaF_2$ of the rest;

(2) the true density is 3.16 $g/cm^3$, in the case of $MgF_2$ of 40% by weight or more and less than 70% by weight (referred to as 40-70% by weight) and $CaF_2$ of the rest; and (3) the true density is 3.17 $g/cm^3$, in the case of $MgF_2$ of 10% by weight or more and less than 40% by weight (referred to as 10-40% by weight) and $CaF_2$ of the rest.

In order to achieve the above object, a $MgF_2$—$CaF_2$ binary system sintered body for a radiation moderator according to a first aspect of the present invention is characterized by comprising $MgF_2$ containing $CaF_2$ from 0.2% by weight to 90% by weight inclusive, having a compact polycrystalline structure excellent in radiation moderation performance, especially neutron moderation performance with a bulk density of 2.96 $g/cm^3$ or more.

In the $MgF_2$—$CaF_2$ binary system sintered body for a radiation moderator according to the first aspect of the present invention, the difference between the parts of the organizational structure of the sintered body is small, and the generated quantity of melt is restricted and the crystal growth of a solid solution (a phase in which a solid phase and a liquid phase are mixed) is suppressed, leading to reducing the occurrence of brittle portions, resulting in enhanced strength of the sintered body. As a result, a sintered body having excellent moderation performance as a neutron moderator and enhanced mechanical strength, that is, all the characteristics required for a neutron moderator, can be obtained.

The $MgF_2$—$CaF_2$ binary system sintered body for a radiation moderator according to a second aspect of the present invention is characterized by having a bending strength of 15 MPa or more and a Vickers hardness of 90 or more as regards mechanical strengths.

The $MgF_2$—$CaF_2$ binary system sintered body for a radiation moderator according to the second aspect of the present invention has strong cohesion between particles, leading to high micro strength of the bonding part, noticeably improved mechanical strength. Accordingly, a sintered body having more excellent moderation performance as a neutron moderator and being extremely excellent in mechanical strength, can be provided.

A method for producing a $MgF_2$—$CaF_2$ binary system sintered body for a radiation moderator according to a first aspect of the present invention is characterized by comprising the steps of:

mixing a $MgF_2$ powder with a $CaF_2$ powder of 0.2-90% by weight and further adding 0.02-1% by weight of a sintering aid thereto to mix;

molding the raw material powder compounded in the preceding step at a molding pressure of 5 MPa or more using a press molding device;

molding the press molded article at a molding pressure of 5 MPa or more using a cold isostatic pressing (CIP) device;

conducting preliminary sintering by heating the CIP molded article in a temperature range of 600° C.-700° C. in an air atmosphere;

conducting sintering by heating the preliminary sintered body in a temperature range from (Tn-100)° C. to (Tn)° C. when the starting temperature of foaming of the preliminary sintered body is (Tn)° C., in an air atmosphere or in an inert gas atmosphere; and forming a sintered body having a compact structure by heating the same in a temperature range of 900° C.-1150° C. in the same atmosphere as the preceding step.

According to the method for producing a $MgF_2$—$CaF_2$ binary system sintered body for a radiation moderator according to the first aspect of the present invention, the sintered body fired by this method has strong cohesion between particles, and high micro strength of the bonding part. The mechanical strength which was a problem to be solved is remarkably improved, and the sintered body can be used as a member for a neutron moderator without problems for actual use.

The degree of compactness of the sintered body can be raised according to the selection of the mix proportion of $MgF_2$—$CaF_2$, heating atmosphere, heating temperature pattern and the like.

The crystalline structure of the sintered body fired by this method is polycrystalline, resulting in remarkable improvement of the brittleness compared with a single crystal.

And the highest attained relative density thereof within a range of good sintering conditions can be raised compared with a sintered body of $MgF_2$ simple, and by making wider the temperature limits of the secondary sintering temperature thereof, in which the bulk density thereof becomes high, the stable sintering conditions can be easily realized.

The method for producing a $MgF_2$—$CaF_2$ binary system sintered body for a radiation moderator according to a second aspect of the present invention is characterized by the shape of a particle size distribution curve of the compound which shows a sub-1-peak-type or 1-peak-type particle size distribution, wherein the maximum particle diameter is 50 μm or less and the median diameter of the particles is 6 μm or less in the method for producing a $MgF_2$—$CaF_2$ binary system sintered body for a radiation moderator according to the first aspect of the present invention.

According to the method for producing a $MgF_2$—$CaF_2$ binary system sintered body for a radiation moderator according to the second aspect of the present invention, by more pulverizing the starting raw material and making the particle size range smaller so as to raise the packing density, the sintering reaction, especially low-temperature sintering which promotes cohesion of particles through solid phase reaction and bonding thereof can be promoted. Accordingly, the mechanical strength of the sintered body fired by this method can be remarkably enhanced.

The method for producing a $MgF_2$—$CaF_2$ binary system sintered body for a radiation moderator according to a third aspect of the present invention is characterized by the inert gas atmosphere in the sintering step comprising one kind of gas or a mixture of plural kinds of gases, selected from among nitrogen, helium, argon and neon in the method for producing a $MgF_2$—$CaF_2$ binary system sintered body for a radiation moderator according to the first or second aspect of the present invention.

By the method for producing a $MgF_2$—$CaF_2$ binary system sintered body for a radiation moderator according to the third aspect of the present invention, defoaming in the sintering process becomes easy to occur, and the relative density of the sintered body is easily raised.

BRIEF DESCRIPTION OF DRAWINGS

FIG. 6 is a table (Table 1) showing the measurement results of the neutron moderation performance of $MgF_2$—$CaF_2$ binary system sintered bodies having varied raw material mix proportions; and FIG. 7 is a table (Table 2) showing measured data of Examples and Comparative Examples.

DESCRIPTION OF EMBODIMENTS

The preferred embodiments of the $MgF_2$—$CaF_2$ binary system sintered body for a radiation moderator having a compact polycrystalline structure excellent in radiation moderation performance, especially neutron moderation performance, and the method for producing the same according to the present invention are described below by reference to the Figures.

Figure 3:
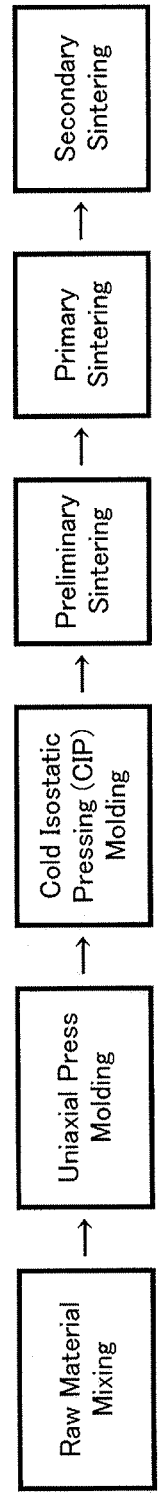
FIG. 3 is a diagram showing a flow of steps for producing a $MgF_2$—$CaF_2$ binary system sintered body.

In the method for producing a $MgF_2$—$CaF_2$ binary system sintered body according to the preferred embodiment, as shown in FIG. 3, a high-purity (purity of 99.9% by weight or more) $MgF_2$ powder was mixed with a high-purity (purity of 99.9% by weight or more) $CaF_2$ powder in the proportion of 0.2-90% by weight (included in a total of 100), and as a sintering aid, for example, a carboxymethyl cellulose (CMC) solution was added thereto in the proportion of 0.02-1% by weight (not included in 100) to 100 of the mixture and mixed. The mixture was used as a starting raw material (raw material mixing step).

The starting raw material was molded at a molding pressure of 5 MPa or more using a uniaxial press device (uniaxial press molding step), and this press molded body was molded at a molding pressure of 5 MPa or more using a cold isostatic pressing (CIP) device (CIP molding step).

Preliminary sintering was conducted by heating this CIP molded body in a temperature range of 600° C.-700° C. in an air atmosphere (preliminary sintering step).

This preliminary sintered body was heated in a temperature range just below the starting temperature of foaming Tn, that is, in a temperature range from (Tn-100° C.) to Tn for a relatively long period of time (specifically, 3-12 hours) in an air atmosphere or in an inert gas atmosphere so as to allow sintering to make progress more uniformly (primary sintering step).

The temperature range just below the starting temperature of foaming Tn was defined through the measurement using a differential thermal analyzer, and the temperature range varies in a range of about 750° C.-900° C. depending on the mix proportion of the raw materials of $MgF_2$ and $CaF_2$. As described above, it varies in a temperature range of 750° C.-850° C. in the case of a composition mainly comprising $MgF_2$, in that of 800° C.-900° C. in the case of a composition mainly comprising $CaF_2$, and in that of 775° C.-875° C. in the case of an intermediate composition of the both.

Figure 2:
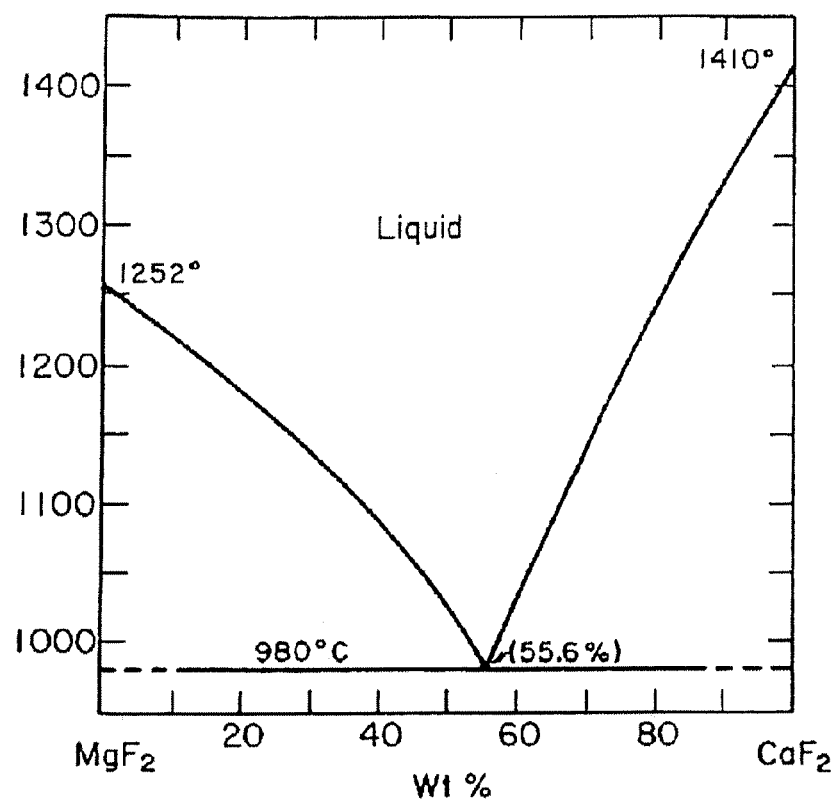
FIG. 2 is a phase diagram of the $MgF_2$—$CaF_2$ binary system.

Thereafter, in the same atmosphere, the same was heated in the vicinity of the temperature limits in which a solid solution starts to be formed (the temperature limits in the vicinity of 980° C., being a temperature at which a solid solution starts to be formed in the phase diagram of the $MgF_2$—$CaF_2$ binary system in FIG. 2), that is, in a temperature range of 900° C.-1150° C. for a relatively short period of time (0.5-8 hours), and then cooled so as to produce a $MgF_2$—$CaF_2$ binary system sintered body having a compact structure (secondary sintering step).

The reason why the sintering step was divided into two steps, primary and secondary, is in order to suppress foaming as much as possible, and make the difference of the degree of sintering progress in every part (such as a periphery portion and a center portion) of the sintered body as small as possible.

Particularly, in order to produce a large-size compact sintered body, the technique is important. The large size here is applied to press molded bodies in the below-described Examples having the size of about 220 mm×220 mm×H85 mm, while the small size is applied to the below-mentioned press molded bodies having the size of dia. 80 mm×H50 mm.

In a test conducted in order to roughly grab proper heating conditions of the sintering step, the starting raw materials comprising $MgF_2$—$CaF_2$ binary system and $MgF_2$ simple, respectively, were used, the sample size was the above large size, and both of the two stages of sintering were conducted in a nitrogen gas atmosphere. In the primary sintering, the temperature was held at 840° C. for 6 hours and in the subsequent secondary sintering, the heating time was set to be 2 hours with varied heating temperatures so as to measure the relative densities of the sintered bodies.

Figure 4:
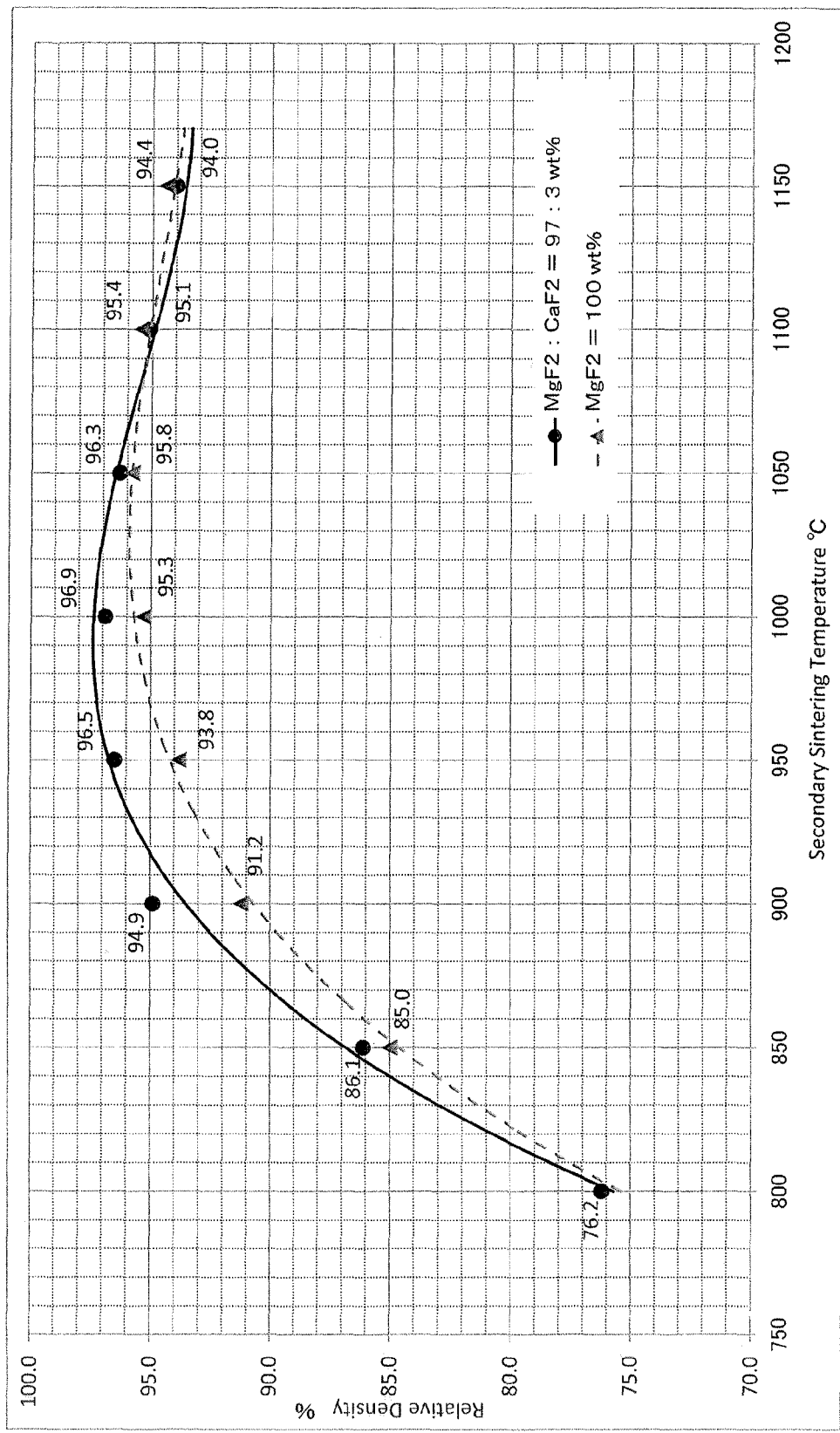
FIG. 4 is a diagram showing the relationship between the secondary sintering temperatures and the relative densities of $MgF_2$—$CaF_2$ binary system sintered bodies and sintered bodies of $MgF_2$ simple.

As a result, as shown in FIG. 4, the relative densities of 95% or more could be secured in a wide range of heating conditions when two-stage sintering step was conducted, in either case of $MgF_2$—$CaF_2$ binary system and $MgF_2$ simple, and particularly, in the case of $MgF_2$—$CaF_2$ binary system, those of 96%-97% could be obtained in the good condition range (heating at 950° C.-1050° C.).

On the other hand, as shown in the below-described Comparative Examples 11 and 12, when only one-stage sintering step was conducted, the relative densities were 94% or less.

The aim of mixing a $CaF_2$ powder being a secondary raw material into a $MgF_2$ powder being a main raw material is to cause the sintering reaction which allows the region of the formation of a solid solution on the phase diagram shown in FIG. 2 to become clearer, since $MgF_2$ simple has a high melting point of 1252° C. and the temperature region of the formation of a solid solution is partially unclear, shown with dot lines.

By mixing the right quantity of $CaF_2$, being a fluoride of Ca which is presumed to have similar characteristics to Mg since Ca belongs to the same group as Mg on the periodic table of elements and its period is next to Mg, the melting point can be lowered and the temperature conditions of the formation of a solid solution can be clarified. By mixing $CaF_2$, the melting point can be moved from the dot line region on the left end portion of the line indicating the temperature region of starting of the formation of a solid solution in FIG. 2 toward the solid line region of the intermediate mix proportions positioned on the right hand. As a result, it becomes easy to make the sintering temperature conditions proper. As a material to be mixed into $MgF_2$ other than $CaF_2$ being a fluoride of Ca, LiF being a fluoride of Li can be exemplified.

As the sintering aid, two kinds, the CMC and the calcium stearate (SAC), were selected. With various adding proportions of each of them, the effects of addition thereof were confirmed. For comparison, a test with no sintering aid was also conducted.

The main raw material $MgF_2$ were mixed with the secondary raw material $CaF_2$ in various mix proportions in a range of 0-97.5% by weight (included in a total of 100). After mixing using a ball mill for half a day, the two kinds of sintering aids were added in the proportion of 0-2% by weight (not included in the total), respectively. And using a pot mill, the same was mixed a whole day and night so as to obtain a starting raw material.

The ball mill made of alumina having an inside diameter of 280 mm and a length of 400 mm was used, and balls of $\phi$5: 1800 g, $\phi$10: 1700 g, $\phi$20: 3000 g and $\phi$30: 2800 g, made of alumina were filled therein. The pot mill made of alumina having an inside diameter of 200 mm and a length of 250 mm was used.

This compound of a prescribed quantity was filled into a wooden mold form, and using a uniaxial press device, compressed and molded at a uniaxial press pressure of 5 MPa or more. The inside size of the mold form used in the Examples was 220 mm×220 mm×H150 mm, and the inside size of the mold form used in a small-size test was 80 mm in diameter and 100 mm in height.

This press molded body was put into a thick vinyl bag, which was then deaired and sealed, and it was put through a cold isostatic pressing (CIP) device. The press molded body was put into a molding part having a two-split structure (inside diameter 350 mm×H120 mm), which was sealed. The space between the vinyl bag with the press molded body inside and the molding part was filled with clean water, and then, isostatic pressing was conducted at a hydraulic pressure of 5 MPa or more so as to form a CIP molded body.

The preliminary sintering step was conducted on the CIP molded bodies in an air atmosphere with various kinds of conditions in a heating temperature range of 500° C. to 750° C. and in a heating time range of 3 to 18 hours.

After observing the appearance of the preliminary sintered bodies, the preliminary sintered bodies were sintered with the conditions which were regarded as good sintering conditions in the preceding preliminary test. The sintering step was conducted with the conditions wherein, in a nitrogen gas atmosphere, the temperature was raised from room temperature to 600° C. at a fixed rate for 6 hours, and held there for 8 hours, and then, it was raised to 1000° C. at a fixed rate for 2 hours and held there for 1 hour. And thereafter, it was lowered to 100° C. for 20 hours.

By observing the appearance of the taken-out sintered bodies, the state of compactness of the inside thereof and the like, proper raw material mix proportions, raw material processing conditions, preliminary sintering conditions and the like were investigated.

As a result, in cases where the mix proportion of the secondary raw material $CaF_2$ to the main raw material $MgF_2$ was less than 0.2% by weight, the sintering performance did not become much better due to mixing of $CaF_2$. The difference in compactness between the inside portion and the periphery portion of the sintered body was likely to be large as is the case with $MgF_2$ simple. Therefore, in order to improve the sintering performance by mixing thereof, it was judged that $CaF_2$ of 0.2% by weight or more was required.

On the other hand, in the case of 90.1% by weight or more, a larger number of large bubbles were left in the inside portion of the sintered body, compared with the periphery portion thereof, resulting in insufficient compactness.

Judging from these situations, the mix proportions of $CaF_2$ to $MgF_2$, in which the difference in compactness between the inside portion and the periphery portion of the sintered body was small, that is, the sintering performance was in a good state, were 0.2-90% by weight. It was confirmed that the more desirable mix proportions thereof in which the difference in compactness between the inside portion and the periphery portion of the sintered body was smaller, resulting in an excellent degree of uniformity, were 1.5-80% by weight. Hence, the proper range of mix proportions of $CaF_2$ was judged to be 0.2-90% by weight, more desirably 1.5-80% by weight.

There was no big difference between the effects of the two kinds of sintering aids, but when the mix proportion of the sintering aid was less than 0.02% by weight, the shape keeping performance of the molded body was poor. And when the mix proportion thereof exceeded 1.1% by weight, coloring which appeared to be a residual of the sintering aid was noticed on the preliminary sintered body or the sintered body in some cases. Hence, the proper range of mix proportions of the sintering aid was judged to be 0.02-1% by weight.

In a uniaxial press test using the above wooden mold form for a small-size test, when the molding pressure of the uniaxial press device was less than 5 MPa, the press molded body easily lost its shape in handling. As the molding pressure was gradually increased from 5 MPa, the bulk density of the press molded body gradually increased, and it was recognized that the bulk densities of the preliminary sintered body and the sintered body also tended to increase though slightly. The test was conducted with the molding pressure gradually increased to 100 MPa. However, even if the molding pressure was raised to 20 MPa or more, no improvement of performance of the preliminary sintered body or the sintered body was recognized. Hence, the proper value of the molding pressure of the uniaxial press device was decided to be 5 MPa or more, desirably 20 MPa.

When the molding pressure of the CIP device was less than 5 MPa, the CIP molded body easily lost its shape in handling. As the molding pressure was gradually increased from 5 MPa, the bulk density of the CIP molded body gradually increased, and it was recognized that the bulk densities of the preliminary sintered body and the sintered body also tended to increase though slightly. The test was conducted with the CIP molding pressure gradually increased to 60 MPa. However, even if the molding pressure was raised to 20 MPa or more, no great improvement of performance of the preliminary sintered body or the sintered body was recognized. Hence, the proper value of the molding pressure of the CIP device was decided to be 5 MPa or more, desirably 20 MPa.

The research of preliminary sintering conditions of the CIP molded body in an air atmosphere was conducted under the below-described conditions. By mixing $MgF_2$ with $CaF_2$ of 3% by weight, and adding CMC of 0.1% by weight as a sintering aid thereto, a starting raw material was prepared. Using the wooden mold form for a small-size test, by setting the molding pressure of a uniaxial press device to be 20 MPa and setting the molding pressure of a CIP device to be 20 MPa, CIP molded bodies were formed. Using the CIP molded bodies formed under such conditions, the preliminary sintering conditions were researched.

At heating temperatures of less than 600° C., shrinkage was small compared with the size of the molded body, while at heating temperatures of 710° C. or more, the shrinkage rate was too high and therefore, shrinkage was difficult to control. Hence, the proper range of the preliminary sintering temperatures was decided to be 600° C.-700° C.

Concerning the heating time, at 600° C., it was judged that 8-9 hours were optimal, and that 4-10 hours were proper, judging from the evaluation of the shrinkage rate. At 700° C., it was judged that 6-8 hours were optimal, and that 4-10 hours were proper. From these results, the heating conditions in the preliminary sintering step were decided to be at 600° C.-700° C. for 4-10 hours in an air atmosphere.

What is likely to give most influence on the performance of a sintered body in producing the $MgF_2$—$CaF_2$ binary system sintered body for a radiation moderator is the sintering step. From the above researches and tests, the proper conditions until just before the sintering step were clarified.

The sintering step and the sintering mechanism which appear to be desirable to a $MgF_2$—$CaF_2$ binary system sintered body for a radiation moderator are put in order.

The terms "primary flocculation process" and "secondary flocculation process" which express the degrees of progress of the sintering step, are described below. The "primary flocculation process" refers to an event in the first half of the stage of sintering, and in the initial stage thereof, the intervals between particles gradually become narrower and the voids among particles also become smaller. With further progress of sintering, the particle-to-particle contact portions become thick and the voids among them become further smaller. Here, the majority of the voids are open pores connecting to the surrounding atmosphere. Up to this stage is called "primary flocculation process".

On the other hand, after the end of the primary flocculation process, with further progress of sintering, the open pores gradually decrease and turn into closed pores. Roughly, the stage of turning into closed pores and the subsequent stage of defoaming and compacting are generically called "secondary flocculation process".

In the producing method according to the preferred embodiment, due to raw material mixing, particle size control, mixing, two-stage molding (uniaxial press molding and CIP molding), preliminary sintering and the like, it was noticed that the voids among particles of the preliminary sintered body were small, and that the voids almost uniformly scattered without gathering (the first half stage of the primary flocculation process).

In the heating process of the next sintering step, the heating temperature is gradually raised. Around the temperature limits (500° C.-550° C.) slightly lower than the preliminary sintering temperatures (600° C.-700° C.), particles start to gather, and thereafter, solid phase reaction starts in the temperature limits far lower than 980° C. at which a solid solution starts to be formed. With that, flocculation of particles makes progress, leading to shorter particle-to-particle distances and smaller voids.

It is generally said that the solid phase reaction starts in the temperature limits lower by the order of 10% or further lower than the temperature at which a solid solution starts to be formed. From the observation results in the preliminary test by the present inventors, it was considered that the solid phase reaction started in far lower temperature limits than the above generally said temperature limits, in the order of 500° C.-550° C.

It can be said on the ground that at 600° C., the lowest limit of the preliminary sintering temperature, sintering by the solid phase reaction has already made progress considerably so that the preliminary sintered body considerably shrinks compared with the CIP molded body.

It is considered that the solid phase reaction makes progress at a low reaction rate in the temperature limits and that it makes progress at a quite high reaction rate in the temperature limits in the vicinity of 750° C., or more up to 980° C. Here, in the case of heating at relatively low temperatures (600° C.-700° C.) like assumed preliminary sintering for a short period of time, most of the voids remain in a state of open pore (which is the first half stage of the primary flocculation process).

What attention should be paid to here is behavior of fine bubbles (foaming bubbles) generated through vaporization of part of the raw material in the temperature limits of about 850° C.-900° C. or more, as mentioned above. In the case of heating at about 1000° C. or more, the heating time should be as short as possible, since this formation of foaming bubbles comes to be noticeable.

In the producing method according to the preferred embodiment, the sintering step is divided into two. In the primary sintering step, by heating in the relatively low temperature limits in which no foaming bubbles are formed for a long period of time, sintering of the whole body is allowed to make progress almost uniformly. The micro structure of the sintered body comprises mainly open pores, but part of them is turned into closed pores (after finishing the second half stage of the primary flocculation process, partially in the secondary flocculation process).

In the secondary sintering step, heating is conducted in the relatively high temperature limits in the vicinity of 980° C. at which a solid solution starts to be formed for a minimum required period of time. As the micro structure of the sintered body, the formation of foaming bubbles is suppressed as much as possible, while the sintering reaction is allowed to make progress so as to turn almost all the open pores into closed pores, that is, the secondary flocculation process is finished, resulting in obtaining a high-density sintered body.

Micro behavior of raw material particles is described here. It is presumed that particles of $CaF_2$ are present around particles of the main raw material $MgF_2$ and promote interface reaction with the particles of $MgF_2$. Around a heating temperature exceeding 980° C. at which a solid solution starts to be formed, melting starts in the vicinity of a particle interface where the particles of $CaF_2$ are present, and a solid solution of a $MgF_2$—$CaF_2$ binary system compound starts to be formed. It is presumed that this solid solution fills the voids among particles and that in some part, finer voids are also filled therewith through capillary phenomenon.

On the other hand, even if the heating temperature is lower than 980° C., by heating and holding at about 750° C. or more for a relatively long period of time as described above, the solid phase reaction easily makes progress, the voids gradually decrease with the elapse of time so as to be closed pores. Parallel with that, a gas component within the closed pores diffuses within the bulk (parent) of the sintered body, leading to the progress of defoaming so as to make the sintered body compact with few bubbles (which is the secondary flocculation process).

Also here, in heating at temperatures not lower than the starting temperature of foaming Tn (the starting temperature of foaming differs depending on the mix proportion of the raw materials $MgF_2$ and $CaF_2$), that is, temperatures exceeding 850° C.-900° C., attention should be paid to the formation of fine bubbles (foaming bubbles) generated through vaporization of the raw material. That is because it is presumed that the foaming bubbles contain fluorine gas, and it is considered that this gas is a relatively heavy element and difficult to diffuse in the bulk of the sintered body. As measures for that, to avoid heating in the temperature limits of vaporization as much as possible, and if necessary, to heat at a temperature as low as possible or to heat for a short period of time are considered.

The difference in appearance between such foaming bubbles and bubbles left after pores became closed but could not be defoamed in the sintering step (hereinafter, referred to as residual bubbles) is described below. The sizes of the foaming bubbles generated by general heating for a relatively short period of time are approximately several μm in diameter, and the shapes thereof are almost perfect spheres.

On the other hand, the shapes of the residual bubbles are not perfect spheres but irregular, and the sizes thereof are all mixed up, large, medium and small. Therefore, it is possible to distinguish the both according to the difference in shape. Here, in the case of high-temperature heating at temperatures far exceeding 1160° C., or heating at temperatures exceeding 1160° C. for a long period of time, a foaming bubble and a foaming bubble, or a residual bubble and a foaming bubble gather and grow to a large irregular bubble in some cases, resulting in difficulty in judging its origin.

With the progress of the secondary flocculation process, the voids among particles become smaller, and all or most of the voids are surrounded by particles or a bridge portion of the sintered body so as to be closed pores (bubbles). Or depending on the conditions, gases are released through the voids (open pores), or gases within the bubbles permeate into the bulk (parent) such as the particles or the bridge portion of the sintered body to degas, resulting in no bubbles (referred to as a defoaming phenomenon).

Whether the voids among particles are left as closed pores, that is, bubbles, or by degassing, no bubbles are formed, is a significant element for deciding the degree of achievement of compactness of the sintered body, leading to deciding the characteristics of the sintered body.

Particularly in the case of sintering in a light element gas atmosphere such as He or Ne among inert gases, it is considered that the lighter element more easily diffuses within the pores or the bulk of the sintered body, leading to promoting the capillary phenomenon and defoaming phenomenon, so that bubbles are difficult to remain, leading to easy compacting.

Thus, in order to make the whole compact, it is important to advance the primary flocculation process (in detail, it is presumed that the primary flocculation process is divided into the first half stage and the second half stage) and the secondary flocculation process almost simultaneously and almost uniformly on the whole in each process.

In the invention according to the preferred embodiment, the preliminary sintering step chiefly equivalent to the first half stage of the primary flocculation process, the primary sintering step chiefly equivalent to the second half stage of the primary flocculation process, and the secondary sintering step chiefly equivalent to the secondary flocculation process are separately conducted, so as to make the two flocculation processes easy to make progress almost uniformly throughout the sintered body.

However, Even if the sintering step is divided into two steps of preliminary sintering and sintering like this, a noticeable difference in degree of compactness is caused without proper heating conditions. For example, in the case of heating at high temperatures exceeding the proper limits in the preliminary sintering step, in the case of rapidly heating at the temperature raising stage of the sintering step, or in cases where the holding temperature in the sintering step is a high temperature exceeding the proper limits, a remarkable difference in degree of compactness is caused between the periphery portion and the inside portion of the sintered body. By improper heating, degassing becomes difficult in the process of compacting of the inside portion of the sintered body, and the compactness of the inside portion thereof is likely to be insufficient.

It means that it is important to make the heating temperature pattern in the sintering step proper according to the size. Particularly, when producing a large-size sintered body, it is necessary to strictly control the heating conditions since a difference in degree of compactness between the periphery portion and the inside portion of such sintered body is easily caused.

In order to clarify the relationship between the sample size and the sintering state, the present inventors conducted a small-size test using samples molded in a mold form of a uniaxial press device the inside size of 80 mm in diameter and 100 mm in height, and a large-size test using samples molded in a mold form thereof the inside size of 220 mm×220 mm×H150 mm.

As a result, in the small-size test, there were cases where a high-density sintered body having a relative density exceeding 95% was obtained depending on the heating conditions even if one sintering step was conducted. On the other hand, in the large-size test, with one sintering step, any of the sintered bodies had a low density of less than 94% under the same sintering conditions as the small-size test.

What is important here is that the whole of the preliminary sintered body has already advanced almost uniformly to the first half stage of the primary flocculation. Only preliminary sintered bodies in a state in which the whole body has already advanced to the first half stage of the primary flocculation were provided to these tests of the sintering step.

The description of the sintering step test

A mixture of a main raw material $MgF_2$ with $CaF_2$ of 3% by weight, and a raw material of $MgF_2$ simple as a comparative material were used as starting materials. CMC of 0.1% by weight was added thereto as a sintering aid. And using the above mold form for a large-size test, the compounds were molded at a molding pressure of 20 MPa of a uniaxial press device and at a molding pressure of 20 MPa of a CIP device.

The CIP molded bodies were preliminary sintered at 650° C. for 6 hours in an air atmosphere so as to obtain preliminary sintered bodies.

In a nitrogen atmosphere, as primary sintering step, the preliminary sintered bodies were heated to 840° C. and the temperature was held there for 6 hours and then raised to a secondary sintering temperature for 2 hours.

The secondary sintering temperature was varied from 700° C. to 1250° C., at an interval of every 50° C., and the temperatures each were held for 2 hours.

Thereafter, the heating was stopped and the temperature was lowered by self-cooling (so-called furnace cooling) for about 20 hours, and when reaching 100° C. or lower at which time it was previously set to take out the sintered body, it was taken out.

As a result of the sintering test with such two-stage sintering step, as shown in FIG. 3, in the case of a range from 900° C. to 1150° C., most of the bulk densities of the sintered bodies exceeded 2.96 g/cm$^3$, which were high. The true density of the binary system compound was 3.15 g/cm$^3$ and the relative density thereof was 94.0%, while the true density of the raw material of $MgF_2$ simple was also 3.15 g/cm$^3$ and the relative density thereof was also 94.0%.

In either case of sintering temperatures of less than 900° C., and those of 1160° C. or more, the relative densities were lower than 94.0% (the bulk density of 2.96 g/cm$^3$). The sintered bodies of the $MgF_2$—$CaF_2$ binary system raw material tended to have a higher relative density by the order of 0.5%-1.5% than those of $MgF_2$ simple in a range of good sintering conditions.

When observing the sections of those sintered bodies, in the case of sintered bodies sintered at temperatures lower than 900° C., not many but some open pores were noticed in some of them, wherein the bridge width of the sintered portion was narrow, so that it could be regarded as absolutely insufficient progress of sintering.

In the case of sintered bodies sintered at temperatures of 1160° C. or more, especially 1200° C. or more, those had a porous pumiceous structure as if bubbles were innumerably formed inside. Fine bubbles which were almost perfect spheres of several to dozen μm in diameter were observed all over the sintered body and innumerable irregular bubbles (foaming bubbles and aggregates thereof) of 10 μm or more in diameter were found all over the sections.

From another examination using a differential thermal analyzer by the present inventors, it was found out that when heating the compound of $MgF_2$—$CaF_2$ binary system, the weight clearly started to decrease at a temperature of about 800° C.-850° C. (the temperature becomes gradually higher within the temperature range as the mix proportion of $CaF_2$ to $MgF_2$ increases), and that the weight started to drastically decrease at about 850° C.-900° C. This means that a sublimation phenomenon in which $MgF_2$ or $CaF_2$ starts to dissolve/vaporize to generate fluorine starts due to heating at about 800° C.-850° C. or more.

A foaming phenomenon through this fluorine sublimation is noticeably caused by heating at about 850° C.-900° C. or more, and fine bubbles are formed all over the sintered body. The behavior of the foaming bubbles such as defoaming or remaining as bubbles is decided according to the degree of progress of the sintering step, in which portion of the sintered body they were formed and the like. In the primary flocculation process, for example, since the whole sintered body contains mainly open pores, the majority of foaming bubbles can be defoamed through the open pores, leading to few bubbles left. In the secondary flocculation process, since the sintered body contains mainly closed pores, a large number of foaming bubbles cannot be defoamed, leading to remaining as bubbles. To swiftly complete the sintering in the secondary flocculation process leads to suppressing foaming and reducing residual bubbles.

Hence, it is preferable that the transition from the primary flocculation process to the secondary flocculation process should be advanced in the whole sintered body with as small a difference of the degree of progress as possible among the portions thereof. However, it is not easy to undergo the transition from the primary flocculation process to the secondary flocculation process in the whole sintered body without a difference of the degree of progress among the portions thereof.

Then, the present inventors considered the below-described method.

Heating at a relatively low temperature in the temperature limits just below the starting temperature of foaming Tn (850° C.-900° C.), specifically in the temperature limits between (Tn-100° C.) and Tn for a relatively long period of time was conducted, so that the primary flocculation process and the first half of the secondary flocculation process were completed. And then, by heating at a temperature in the vicinity of the temperature (980° C.) at which a solid solution starts to be formed for a relatively short period of time, the second half of the secondary flocculation process was completed. By such sintering, the degree of progress of sintering could be made uniform in the whole sintered body, and the formation of bubbles could be suppressed as much as possible.

How the proper sintering conditions were decided is described below.

In the same manner as the above sintering condition change test, a main raw material $MgF_2$ was mixed with $CaF_2$ of 3% by weight. CMC of 0.1% by weight was added thereto as a sintering aid. The same was molded using a mold form for a large-size test at a molding pressure of 20 MPa of a uniaxial press device and a molding pressure of 20 MPa of a CIP device. Preliminary sintering was conducted on this CIP molded body at 650° C. which was held for 6 hours in an air atmosphere.

As the conditions of the sintering step, the atmosphere was set to be a nitrogen gas atmosphere. Preliminary tests concerning each of heating and cooling conditions in the heating pattern were conducted in three cases of the required time of 4, 6 and 8 hours. As a result, in the case of 4 hours, small cracks occurred in the sintered body, while in the other cases, the results were good. Therefore, the required time was set to be 6 hours, shorter one selected from 6 and 8 hours.

The atmosphere was set to be a nitrogen gas atmosphere, and the heating temperature was varied in a range of 700° C. to 1250° C. In eleven cases of the holding time of 2, 3, 4, 5, 6, 8, 10, 12, 14, 16 and 18 hours, the tests were conducted.

As a result, in the case of less than 750° C., the compactness was insufficient, regardless of the holding time. In the case of heating at 750° C., the compactness was insufficient with a holding time of 4 hours or less. On the other hand, in the case of heating at 1160° C. or more, a large number of bubbles were generated due to too fast sintering speed, regardless of the holding time. In the case of a holding time of 18 hours, in some cases, foaming occurred in part of the periphery of the sintered body, leading to getting out of shape in appearance.

Reviewing the results, in the case of heating at 750° C., the sintering state was good with a holding time of 14 and 16 hours.

In the case of heating at 800° C., the sintering state was good with a holding time of 10 and 12 hours, while slightly insufficient with 6 and 8 hours, and beyond decision of quality with 14 hours or more.

In the case of 830° C., the sintering state was good with a holding time of 10 and 12 hours.

In the case of 850° C., the sintering state was good with a holding time of 8, 10 and 12 hours, while slightly insufficient with 5 hours, and beyond decision of quality with 14 hours or more.

In the case of 900° C., the sintering state was good with a holding time of 5 to 12 hours, while slightly insufficient with 4 hours, and beyond decision of quality with 14 hours or more.

In the case of 1000° C., the sintering state was good with a holding time of 5 to 12 hours, while slightly insufficient with 4 hours, and beyond decision of quality with 14 hours or more.

In the case of 1050° C., the sintering state was good with a holding time of 5 to 10 hours, while slightly insufficient with 4 hours, and much foaming was seen with 12 hours or more.

In the case of 1100° C., the sintering state was good with a holding time of 4 to 8 hours, while slightly insufficient with 3 hours or less, and much foaming was seen with 10 hours or more.

In the case of 1150° C., the sintering state was good with a holding time of 2 and 3 hours, while much foaming was seen with 4 hours or more.

In the case of 1160° C. or more, much foaming was seen with any holding time, and the results were beyond decision of quality or poor because of too much melting.

Here, when the heating temperature was a comparatively low temperature of 750° C. to 850° C., the sintering state was good with a holding time of 6 to 12 hours, while that was slightly insufficient with a holding time of 3 to 5 hours. Since the method according to the preferred embodiment has the subsequent secondary sintering step, with the evaluation in this step (equivalent to the primary sintering step), the holding time of 3-12 hours was regarded as a good heating condition.

In order to examine the relationship between the heating temperature and the bulk density of the sintered body, using the same preliminary sintered bodies as the above, the heating temperature was varied within a range of 600° C. to 1300° C. (with a holding time of 6 hours in any case).

As a result, in the case of a heating temperature of 850° C., the bulk density was approximately 2.96 g/cm$^3$ (the relative density of 94.0%). The sintered body having a bulk density of that value or more was judged to have sufficient compactness without troubles such as losing its shape in the treatment of the second step. On the other hand, in the case of heating temperatures of 1160° C. or more, in some cases, foaming occurred in part of the periphery of the sintered body, resulting in a trouble such as getting out of shape in appearance.

From the above examination results of the sintering conditions and the relationship between the heating temperature and the bulk density, it was judged that, if the sintering step was one heating step, the heating temperature of 850° C. to 1150° C. and the holding time of 3 to 12 hours were proper.

What was clarified here is, when relatively long time heating, such as at 900° C. for 14 hours or more, at 1000° C. for 14 hours or more, at 1100° C. for 10 hours or more, or at 1150° C. for 8 hours or more, was conducted, a large number of foaming bubbles were generated and part of those gathered and grew to large bubbles. Such sintered body involved defects which would cause cracks to occur from a large bubble portion or cause splitting in processing of the next mechanical processing step.

From these situations, as a fundamental plan of the sintering step, it was decided that foaming should be suppressed as much as possible, and the sintering reaction should be allowed to sufficiently make progress, leading to producing a sintered body having a good processability in the subsequent mechanical processing step.

At the first stage of the sintering step (the primary sintering step), it was aimed to suppress foaming to a minimum, to allow the sintering to make slow progress, and to minimize a difference of the degree of progress between the inside portion and the periphery portion of the sintered body.

Therefore, the heating temperature was decided to be within the above range of 700° C. to 1150° C. Since the starting temperature of foaming Tn is 850° C. in the case of a raw material mainly comprising $MgF_2$, it was judged that the heating temperature should be 850° C. or less, not exceeding the temperature. On the other hand, since the sintering state was insufficient in the case of heating at temperatures lower than the Tn by 100° C. or more, it was judged that the heating temperature at the first stage of the sintering step should be between (Tn-100° C.) and Tn, between 750° C. and 850° C. in the case of a raw material mainly comprising $MgF_2$.

The proper heating conditions in the primary sintering step were the heating temperature between (Tn-100° C.) and Tn, and the holding time of 3-12 hours. The same tendency was found even in cases where the mix proportion of $CaF_2$ to $MgF_2$ varied between 0.5-90% by weight.

Heating at the stage of enhancing the sintering reaction of the sintered body, that is, heating in the secondary sintering step, was decided to be conducted properly in the temperature limits in the vicinity of 980° C. at which a solid solution starts to be formed, that is, 900° C. to 1150° C. It was aimed to make the holding time as short as possible in order to enhance the sintering reaction and suppress foaming. The proper holding time was decided to be 0.5 to 8 hours, since the enhancement of the sintering reaction was poor in the case of less than 0.5 hour, and too many bubbles were formed in the case of 9 hours or more.

The examination of the proper conditions of the heating temperature and the holding time in the secondary sintering process when the atmospheric gas was changed from nitrogen gas to helium gas is described below.

A mixture of a main raw material $MgF_2$ with $CaF_2$ of 3% by weight was used as a starting material, to which CMC of 0.1% by weight was added as a sintering aid.

Using a mold form of press molding for a large-size test, the material was molded at a molding pressure of 20 MPa of a uniaxial press device and at a molding pressure of 20 MPa of a CIP device. This CIP molded body was preliminary sintered at 650° C. for 6 hours in an air atmosphere so as to obtain a preliminary sintered body.

Using helium gas as the atmospheric gas in the primary and secondary sintering processes, the preliminary sintered body was heated to 840° C. which was held for 6 hours as primary sintering. Then, it was raised to each of secondary sintering temperatures varying in a range of 700° C. to 1250° C., at an interval of every 50° C. for 2 hours, and the target temperature was held for 2 hours. And then, the heating was stopped and the temperature was lowered by self-cooling (so-called furnace cooling) for about 20 hours, and when reached a predetermined taking-out temperature of 100° C. or lower, the sintered body was taken out.

Figure 5:
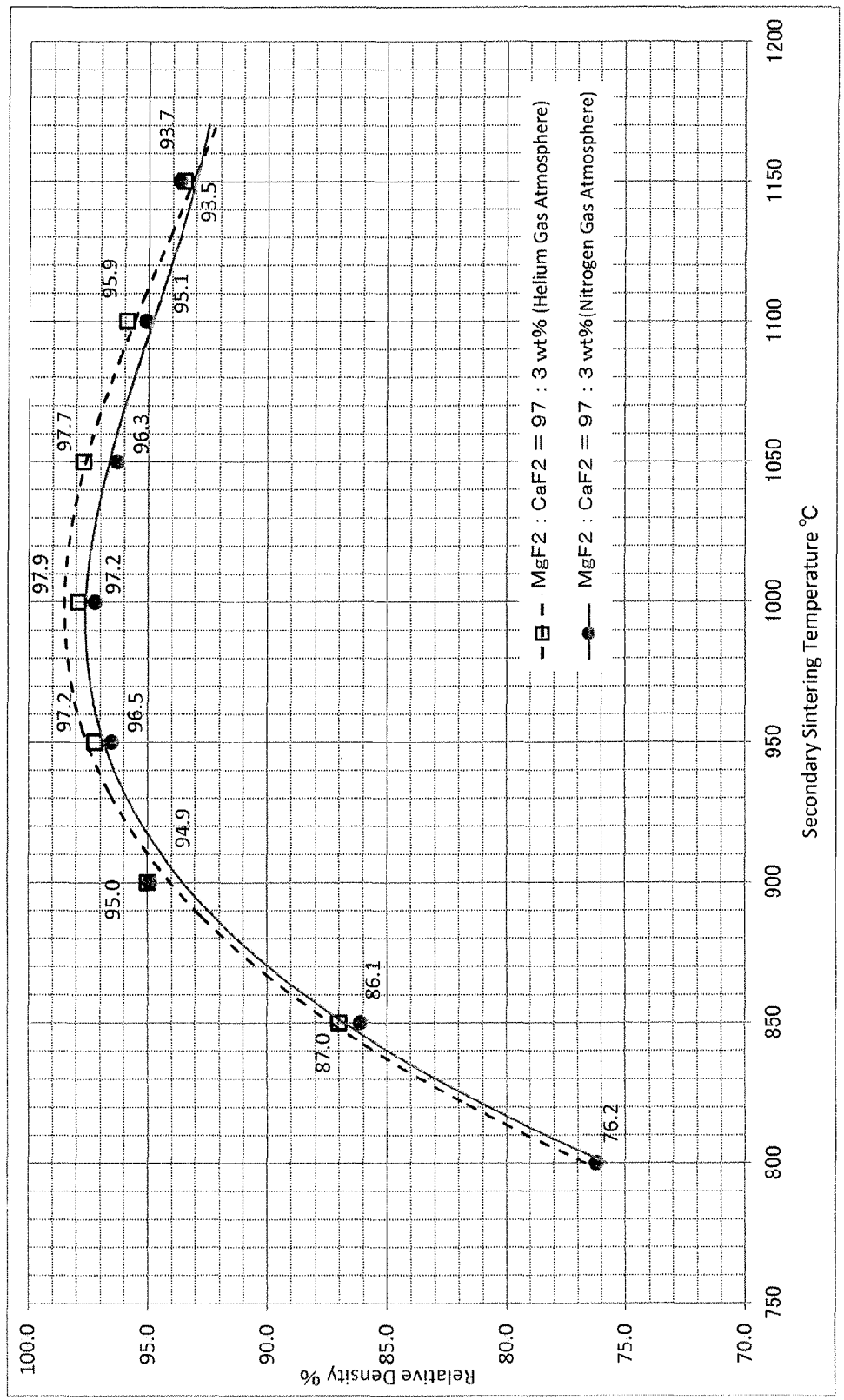
FIG. 5 is a diagram showing the relationship between the secondary sintering temperatures and the relative densities of $MgF_2$—$CaF_2$ binary system sintered bodies in the case of the atmospheric gas in the sintering step switched to nitrogen gas and to helium gas.

As a result of the sintering test with the above two-stage sintering step, as shown in FIG. 5, in the case of a temperature range of 900° C. to 1150° C., most of the sintered bodies had a high bulk density exceeding 2.96 g/cm$^3$. The true density of the binary system compound was 3.15 g/cm$^3$ and the relative density thereof was 94.0%, while the true density of the raw material of $MgF_2$ simple was also 3.15 g/cm$^3$ and the relative density thereof was also 94.0%.

In either case of sintering temperatures lower than 900° C., and those of 1160° C. or more, the relative density was lower than 94.0% (the bulk density of 2.96 g/cm$^3$). The sintered bodies sintered in a helium gas atmosphere tended to have a higher relative density within a range of good sintering conditions by the order of 0.5%-1% than in a nitrogen gas atmosphere.

It is considered that the reason why the bulk density becomes high in a helium gas atmosphere is because the diffusion velocity of helium gas within the bulk (parent) of the sintered body is higher than that of nitrogen gas. It is presumed that, since helium gas more easily diffuses within the bulk than nitrogen gas, when voids become closed pores with the progress of sintering in the sintering process, part of the closed pores disappear without becoming bubbles, or the sizes of the closed pores become smaller.

However, helium gas showed better effects within a range of the above proper sintering conditions, while the effects were not all-around, being not noticeably seen in the region other than the proper sintering conditions.

As the reasons of such result, it was considered that under the sintering conditions outside the proper range, for example, there was a limit in improving too slow sintering speed due to an insufficient heating condition, or in the case of an excessive heating condition, the ununiformity of the sintering speed of every part of the sintered body could not be improved by enhancing the diffusivity of helium gas in the bulk.

In the case of helium gas, when the heating temperature in the sintering step was less than 900° C., regardless of the holding time, or in the case of a holding time of 4 hours or less, the compactness was insufficient. When the heating temperature was 1160° C. or more, the sintering speed was too high, regardless of the holding time, as is the case with nitrogen gas, resulting in occurrence of a large number of bubbles, and in the case of a holding time of 16 hours or more, because of foaming, the appearance got out of shape in some cases.

Accordingly, in the case of a starting raw material made by mixing mainly $MgF_2$ with $CaF_2$, it was judged that the proper range of sintering temperatures was 900° C.-1150° C., regardless of the kind of inert atmospheric gas in the sintering step. Furthermore, in the case of sintering temperatures of 930° C.-1100° C., even when the sintered body was provided to the mechanical processing, structural defects such as cracks were difficult to occur, leading to good mechanical processability. As a result, it was judged that the sintering temperature was more preferably in a temperature range of 930° C.-1100° C.

Therefore, as proper heating conditions of the sintering step in a helium gas atmosphere, as is the case with the above nitrogen gas atmosphere, the proper condition of the primary sintering step was in a range of 750° C. or more and less than the starting temperature of foaming, while that of the secondary sintering step was in a temperature range of 900° C.-1150° C.

The inert gas is not limited to nitrogen and helium. In the case of argon or neon, the same effects can be obtained. Moreover, since neon is expected to have high solubility or high diffusivity in the parent of the sintered body, like helium, the defoaming phenomenon can be more promoted and effects equal to those of helium can be expected.

When the heating conditions of the sintering step were within the proper range, the state of the completed sintered body was wholly compact in any case, and no clearly defective portion such as a locally-found large void or a crack seen in a general ceramic sintered body could be found in this sintered body.

As the particle size control of a $MgF_2$ powder and a $CaF_2$ powder each, using a container of a pot mill made of alumina the size of an inside diameter of 200 mm and a length of 250 mm as a ball mill, balls made of alumina, $\phi$20 mm: 3000 g and $\phi$30 mm: 2800 g, were filled therein. And about 3000 g of each of the raw material powders was filled therein and rotated for a prescribed period of time. The rotation was stopped every two or three days so as to take powder samples and measure the same.

The particle size distribution were measured using 'a laser diffraction particle size analyzer (type number: SALD-2000)' made by Shimadzu Corporation according to JIS R 1629 'Determination of particle size distributions for fine ceramic raw powders by laser diffraction method'. The sample preparation at that time was conducted according to JIS R1622 'General rules for the sample preparation of particle size analysis of fine ceramic raw powder'.

As the light source of the SALD-2000, a semiconductor laser of a wavelength of 680 nm is used. The sensitivity to particles having a diameter larger than this wavelength (about 1 μm or more) was good and the measurement accuracy was high. On the other hand, as for the sensitivity to fine particles of the order of submicron, it was considered that the measurement accuracy was low compared with the particles having a large diameter though some way to improve the measurement accuracy was devised.

Therefore, it is considered that the actual number of fine particles of the order of submicron may be larger than the analysis result. In other words, 'there is a high possibility that the ratio of fine particles may be larger than the analysis result in the actual particle size distribution, and that the mean particle diameter may be smaller than the shown value thereof.' However, in the present application, the values of the particle sizes measured according to the above measurement method are shown as they are.

Figure 1:
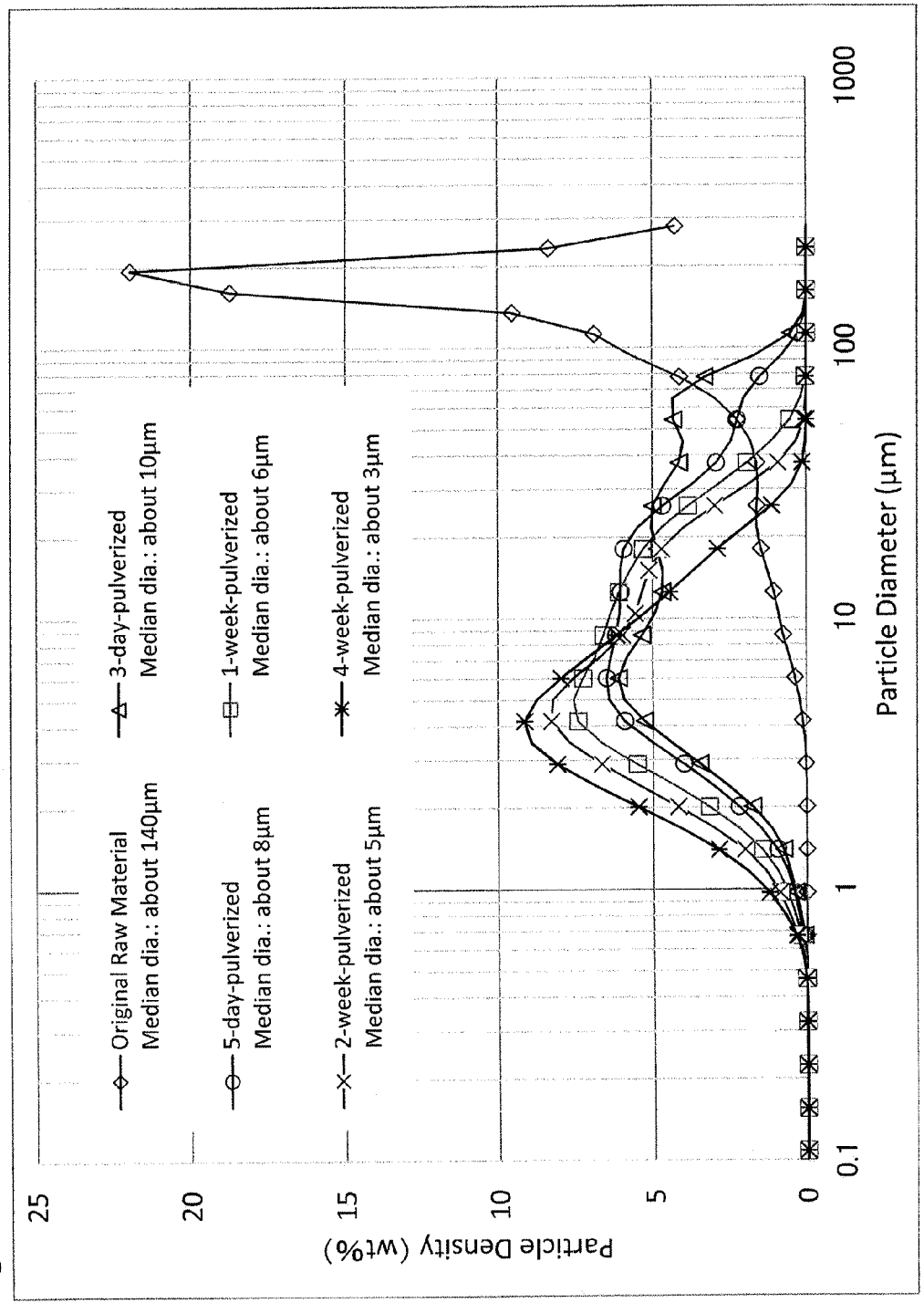
FIG. 1 is a diagram showing an example of a particle size distribution when a raw material of $MgF_2$ simple is pulverized.

FIG. 1 shows a particle size distribution in the case of the above pulverization of a $MgF_2$ raw material. It was found that the median diameter was about 10 µm after three-day pulverization, about 8 µm after five-day pulverization, about 6 µm after one-week pulverization, about 5 µm after two-week pulverization, and about 3 µm after four-week pulverization. Even if a $MgF_2$ raw material and a $CaF_2$ raw material were mixed, the particle size distribution similar to that of the raw material of $MgF_2$ simple could be obtained.

Concerning the original raw material powder and the above particles whose mean particle diameter became about 4 µm after three-week pulverization, the shapes in appearance of the particles of them, respectively, were observed using an electron microscope. In the original raw material powder, some irregular-shaped particles, mainly angular particles were seen, while most of the particles after three-week pulverization were rounded. It was found that most of the angular portions of the particles of the original raw material powder were worn by pulverization so as to be approximated to sphere shapes.

The shape of the particle size distribution curve of the powder after this particle size control can be expressed by being likened to the shape of a mountain range. When the shape of the curve looks like as if "two peaks" or "three peaks" run in a line, it is called '2-peak type' or '3-peak type'. The curve of three-day pulverization and that of five-day pulverization obviously showed a high ratio of coarse particle portions, respectively, which were regarded as '2-peak type' or '3-peak type'. On the other hand, in the case of one-week pulverization and two-week pulverization, respectively, the ratio of the coarse particle portions substantially decreased, the coarse particle portion of 30 µm or more remained several % by weight, but that of 50 µm or more almost disappeared, and the shape of the particle size distribution curve was reaching almost the 1-peak type having a small gently inclined portion around the particle diameter of 10 µm-15 µm (this state is called 'sub-1-peak type'). And in the case of four-week pulverization, the coarse particle portion of 30 µm or more almost disappeared and the shape of the particle size distribution curve could be approximately similar to a normal distribution (this state is called '1-peak type').

Thus, the particle shapes were rounded and approached sphere shapes by pulverization of the raw material powder, and the ratio of coarse particles decreased, resulting in a great change of the shape of the particle size distribution curve from '2-peak type' or '3-peak type' to 'sub-1-peak type', and further to '1-peak type'. This change exerted a noticeably good influence on sintering reaction in the sintering process.

EXAMPLES

Examples according to the present invention are described below by reference to the Figures, but the present invention is not limited to the below-described Examples.

Here, a characteristic evaluation test conducted on sintered bodies is described. Samples for evaluation were prepared by prototyping large-size sintered bodies (rough size of the sintered body: about 205 mm×about 205 mm×H about 70 mm) and conducting mechanical processing such as cut-out in the shape of a required sample thereon.

In order to evaluate the neutron moderation performance, as shown in the above Non-Patent Documents 1 and 2, a beam emitted from an accelerator was allowed to collide with a plate made of Be being a target, and by nuclear reaction, high-energy neutrons (fast neutrons) were mainly generated.

Then, using Pb and Fe each having a large inelastic scattering cross section as a moderator in the first half of moderation, the fast neutrons were moderated to some extent (approximately, up to 1 MeV) while suppressing the attenuation of the number of neutrons.

The moderated neutrons were irradiated to a moderator to be evaluated (a moderator in the second half of moderation), and by examining the neutrons after moderation, the moderator was evaluated.

The examination of the neutrons was conducted according to the method described in the above 'Non-Patent Document 3'.

The moderators to be evaluated were made of raw materials $MgF_2$ and $CaF_2$ in some varied mix proportions. Through the mixing step of each kind of raw materials, molding step and sintering step, a high-density $MgF_2$—$CaF_2$ binary system sintered body having a relative density in a fixed range (95.0±0.5%) was produced. The total thickness of a moderator in the second half was set to be 600 mm in any case.

What was evaluated here is the dose of epithermal neutrons having intermediate-level energy which is effective for therapy, and how many fast neutrons and gamma-rays having high-level energy which has a high possibility of adversely influencing a patient (side effects), remained in the neutrons moderated by the moderator. The results are shown in FIG. 6 (Table 1).

The dose of epithermal neutrons effective for therapy slightly varied, as the quantity of $CaF_2$ mixed into $MgF_2$ was increased, but the digit of the neutron flux (dose) of epithermal neutrons was the ninth power in any case, so that regardless of the mix proportion, the dose thereof sufficient for therapy was secured.

On the other hand, the mix rate of fast neutrons having a high possibility of adversely influencing a patient (the ratio of fast neutron dose in the total neutron dose after passing through a moderator) was the lowest in the case of mixing $CaF_2$ of several to 10% by weight. It gradually increased as the mix proportion thereof far exceeded these mix proportions and increased to 20% by weight, and to 40% by weight. It was the highest when $CaF_2$ was 100% by weight.

The mix rate of gamma-rays having the next highest possibility of adversely influencing a patient after fast neutrons (the ratio of gamma-ray dose in the total neutron dose after passing through a moderator) was a low digit of $E^{-14}$ (the minus 14th power), regardless of the mix proportion of $CaF_2$ to $MgF_2$. The influence of gamma-rays was small, regardless of the mix proportion of $CaF_2$.

From these results, it was proved that when the main raw material $MgF_2$ was mixed with $CaF_2$ of 2-10% by weight, it had the most excellent performance as a moderator. Even if the mix proportion was other than such mix proportions, for example, 0.2% by weight or more and less than 2% by weight, or 10.1% by weight or more and 90% by weight or less, the neutrons were on the level usable for therapy.

The evaluation results are limited to the cases where the relative density of the sintered body is roughly within a fixed range (95.0±0.5%). The higher relative density the sintered body has, the lower the residual dose of fast neutrons is. Conversely, the lower relative density the sintered body has, the higher the residual dose of fast neutrons is. Accordingly, the importance of improvement of the density of the sintered body is the same.

Concerning the moderation performance of a moderator to neutrons, it was sufficient only that a $MgF_2$—$CaF_2$ binary system sintered body having a compact structure should have a bulk density of 2.96 $g/cm^3$ or more.

The moderator to neutrons is required to have mechanical strength other than moderation performance. It was proved by the below-described examination of mechanical strength that the sintered body for a radiation moderator according to the present invention had sufficient mechanical strength, with which it could be used without problems in processing and molding such as cutting-off, grinding, polishing, cleaning and drying as a moderating member in a moderation system device for BNCT, and further in handling such as the installation thereof in the moderation system device. Even if it was irradiated with neutrons, it was capable of resisting their irradiation impacts, being extremely excellent.

As mechanical strengths, bending strength and Vickers hardness were examined. The samples for bending strength, having a size of 4 mm×46 mm×t3 mm with the upper and lower surfaces optically polished were prepared according to JIS C2141, and tested according to the three-point bending test JIS R1601.

To obtain the Vickers hardness, according to JIS Z2251-1992, using 'Micro Hardness Tester' made by Shimadzu Corporation, an indenter having a load of 100 g was pressed for 5 seconds of loading time so as to measure the diagonal length of the impression, which was converted into hardness in the following manner.

$$\text{Vickers hardness} = 0.18909 \times P/(d)^2$$

Here, P: load (N) and d: diagonal length of impression (mm)

Example 1

A high-purity $MgF_2$ powder being a main raw material (mean particle diameter of 4 μm and purity of 99.9% by weight or more) was mixed with a $CaF_2$ powder (mean particle diameter of 4 μm and purity of 99.9% by weight or more) of 1.5% by weight, and mixed using a ball mill for 12 hours. Thereafter, a carboxymethyl cellulose (CMC) solution was added thereto as a sintering aid in the proportion of 0.1% by weight to 100 of the mixture, which was mixed in a pot mill for 12 hours so as to obtain a starting raw material.

This starting raw material was filled into a mold form (inside size of 220 mm×220 mm×H150 mm) of a uniaxial press device and compressed at a uniaxial press pressure of 20 MPa to be molded. This press molded body (size of about 220 mm×220 mm×t85 mm), which was put into a thick vinyl bag and sealed after deairing, was put into a molding part (inside size: dia. 350 mm×H120 mm) of a cold isostatic pressing (CIP) device. Clean water was filled into the space between the vinyl bag with the press molded body therein and the CIP molding part, and by isostatic pressing at a molding pressure of 20 MPa at room temperature, CIP molding was conducted.

The preliminary sintering step was conducted on this CIP molded body at 650° C. for 6 hours in an air atmosphere so as to obtain a preliminary sintered body.

This preliminary sintered body was heated from room temperature to 800° C. at a fixed rate for 6 hours in a nitrogen gas atmosphere, and the temperature was held there for 8 hours. It was then raised to 1050° C. at a fixed rate for 2 hours and held there for 1.5 hours. Heating was then stopped, and the temperature was lowered by self-cooling (so-called furnace cooling) for about 20 hours to 100° C. or less at which time it was previously set to take out the sintered body, after which it was taken out.

The bulk density of the sintered body was calculated at 3.02 $g/cm^3$ (the true density of this compound is 3.15 $g/cm^3$ and the relative density thereof is 95.9%, and hereinafter, referred to as "true density of 3.15 $g/cm^3$ and relative density of 95.9%") from the bulk volume of the appearance thereof and the weight thereof. The sintering state thereof was good.

Since the appearance of the sintered body was a square form, the 'bulk density' here was obtained by a method wherein the bulk volume was calculated from the measured two sides of the square and thickness, and the weight separately measured was divided by the bulk volume. This also applied to the following.

Using a sample taken from this sintered body, evaluation tests of neutron moderation performance and characteristics of every kind were conducted. The results are shown in FIG. 7 (Table 2).

This also applied to the following Examples and Comparative Examples. Here, concerning a sintered body of $MgF_2$ simple and a sintered body of $CaF_2$ simple, being comparative materials, the neutron moderation performance and mechanical strengths were measured like the Examples and Comparative Examples.

The sintered body in Example 1 showed excellent neutron moderation performance, and the mechanical strengths thereof were also good enough not to cause problems in handling in the next step.

Example 2

A $MgF_2$ powder being a main raw material (mean particle diameter of 6 μm and purity of 99.9% by weight) was mixed with a $CaF_2$ powder (mean particle diameter of 6 μm and purity of 99.9% by weight) of 0.2% by weight, and mixed using a ball mill for 12 hours. Thereafter, with the same molding conditions as in the above Example 1, a CIP molded body was produced, and the preliminary sintering step was conducted on this CIP molded body at 640° C. for 6 hours in an air atmosphere so as to obtain a preliminary sintered body.

This preliminary sintered body was heated from room temperature to 800° C. at a fixed rate for 6 hours in a helium gas atmosphere, and the temperature was held there for 5 hours. It was then raised to 920° C. at a fixed rate for 4 hours and held there for 1 hour. Then, the temperature was lowered by furnace cooling to a predetermined taking-out temperature of 100° C., and the sintered body was taken out. The bulk density of the sintered body was 2.97 $g/cm^3$ (true density of 3.15 $g/cm^3$ and relative density of 94.3%). It was rather light, but the sintering state thereof was not unusual in appearance.

Any of the evaluation results of the neutron moderation performance and mechanical strengths were good as shown in Table 2.

Example 3

The same $MgF_2$ powder was mixed with the same $CaF_2$ powder of 2% by weight as those in the above Example 1 and mixed using a ball mill for 12 hours. Thereafter, calcium stearate (SAC) of 1.0% by weight was added thereto as a sintering aid. The compound was mixed in a pot mill for 12 hours so as to obtain a starting raw material.

Using a uniaxial press device, the press molding was conducted at a press pressure of 30 MPa, and then, using a cold isostatic pressing (CIP) device, the CIP molding was conducted at a CIP pressure of 30 MPa. The preliminary sintering step was conducted on this CIP molded body at 700° C. for 6 hours in an air atmosphere so as to obtain a preliminary sintered body.

This preliminary sintered body was heated from room temperature to 840° C. at a fixed rate for 6 hours in an air atmosphere, and the temperature was held there for 8 hours. It was then raised to 1150° C. at a fixed rate for 2 hours and held there for 0.75 hour. The temperature was then lowered by furnace cooling to a predetermined taking-out temperature of 100° C., and the sintered body was taken out. The bulk density of the sintered body was 3.06 g/cm$^3$ (true density of 3.15 g/cm$^3$ and relative density of 97.1%), and the sintering state thereof was good.

Any of the evaluation results of the neutron moderation performance and mechanical strengths were good as shown in Table 2.

Example 4

The same $MgF_2$ powder was mixed with the same $CaF_2$ powder of 3% by weight as those in the above Example 1 and mixed using a ball mill for 12 hours. Thereafter, a CMC solution of 0.03% by weight was added thereto as a sintering aid. The compound was mixed in a pot mill for 12 hours so as to obtain a starting raw material.

Using a uniaxial press device, the press molding was conducted at a press pressure of 30 MPa, and then, using a cold isostatic pressing (CIP) device, the CIP molding was conducted at a CIP pressure of 30 MPa. The preliminary sintering step was conducted on this CIP molded body at 660° C. for 8 hours in an air atmosphere so as to obtain a preliminary sintered body.

This preliminary sintered body was heated from room temperature to 830° C. at a fixed rate for 6 hours in a nitrogen gas atmosphere, and the temperature was held there for 6 hours. It was then raised to 1080° C. at a fixed rate for 2 hours and held there for 2 hours. The temperature was then lowered by furnace cooling to a predetermined taking-out temperature of 100° C., and the sintered body was taken out. The bulk density of the sintered body was 3.07 g/cm$^3$ (true density of 3.15 g/cm$^3$ and relative density of 97.5%), and the sintering state thereof was good.

Any of the evaluation results of the neutron moderation performance and mechanical strengths were good as shown in Table 2.

Example 5

The same $MgF_2$ powder was mixed with the same $CaF_2$ powder of 7.5% by weight as those in the above Example 1 and mixed using a ball mill for 12 hours. Thereafter, calcium stearate (SAC) of 0.07% by weight was added thereto as a sintering aid. The compound was mixed in a pot mill for 12 hours so as to obtain a starting raw material.

Using a uniaxial press device, the press molding was conducted at a press pressure of 40 MPa, and then, using a cold isostatic pressing (CIP) device, the CIP molding was conducted at a CIP pressure of 40 MPa. The preliminary sintering step was conducted on this CIP molded body at 690° C. for 8 hours in an air atmosphere so as to obtain a preliminary sintered body.

This preliminary sintered body was heated from room temperature to 830° C. at a fixed rate for 6 hours in a nitrogen gas atmosphere, and the temperature was held there for 9 hours. It was then raised to 1080° C. at a fixed rate for 2 hours and held there for 2 hours. The temperature was then lowered by furnace cooling to a predetermined taking-out temperature of 100° C., and the sintered body was taken out. The bulk density of the sintered body was 3.06 g/cm$^3$ (true density of 3.15 g/cm$^3$ and relative density of 97.1%), and the sintering state thereof was good.

Any of the evaluation results of the neutron moderation performance and mechanical strengths were good as shown in Table 2.

Example 6

A $MgF_2$ powder being a main raw material (mean particle diameter of 5 μm and purity of 99.9% by weight) was mixed with a $CaF_2$ powder (mean particle diameter of 5 μm and purity of 99.9% by weight) of 18% by weight, and mixed using a ball mill for 12 hours. Thereafter, a CMC solution of 0.3% by weight was added thereto as a sintering aid. The compound was mixed in a pot mill for 12 hours so as to obtain a starting raw material.

Using a uniaxial press device, the press molding was conducted at a press pressure of 6 MPa, and then, using a cold isostatic pressing (CIP) device, the CIP molding was conducted at a CIP pressure of 15 MPa. The preliminary sintering step was conducted on this CIP molded body at 630° C. for 8 hours in an air atmosphere so as to obtain a preliminary sintered body.

This preliminary sintered body was heated from room temperature to 820° C. at a fixed rate for 6 hours in a nitrogen gas atmosphere, and the temperature was held there for 6 hours. It was then raised to 930° C. at a fixed rate for 2 hours and held there for 4 hours. The temperature was then lowered by furnace cooling to a predetermined taking-out temperature of 100° C., and the sintered body was taken out. The bulk density of the sintered body was 2.98 g/cm$^3$ (true density of 3.15 g/cm$^3$ and relative density of 94.6%), and the sintering state thereof was good.

Any of the evaluation results of the neutron moderation performance and mechanical strengths were good as shown in Table 2.

Example 7

The same $MgF_2$ powder was mixed with the same $CaF_2$ powder of 2.5% by weight as those in the above Example 6 and mixed using a ball mill for 12 hours. Thereafter, a CMC solution of 0.1% by weight was added thereto as a sintering aid. The compound was mixed in a pot mill for 12 hours so as to obtain a starting raw material. Using a uniaxial press device, the press molding was conducted at a press pressure of 30 MPa, and then, using a cold isostatic pressing (CIP) device, the CIP molding was conducted at a CIP pressure of 30 MPa. The preliminary sintering step was conducted on this CIP molded body at 650° C. for 6 hours in an air atmosphere so as to obtain a preliminary sintered body.

This preliminary sintered body was heated from room temperature to 840° C. at a fixed rate for 6 hours in a nitrogen gas atmosphere, and the temperature was held there for 5 hours. It was then raised to 1150° C. at a fixed rate for 2 hours and held there for 0.5 hours. The temperature was then lowered by furnace cooling to a predetermined taking-out temperature of 100° C., and the sintered body was taken out. The bulk density of the sintered body was 3.01 g/cm$^3$ (true density of 3.15 g/cm³ and relative density of 95.6%), and the sintering state thereof was good.

Any of the evaluation results of the neutron moderation performance and mechanical strengths were good as shown in Table 2.

Example 8

The same $MgF_2$ powder was mixed with the same $CaF_2$ powder of 50% by weight as those in the above Example 1 and mixed using a ball mill for 12 hours. Thereafter, a CMC solution of 1% by weight was added thereto as a sintering aid. The compound was mixed in a pot mill for 12 hours so as to obtain a starting raw material. Using a uniaxial press device, the press molding was conducted at a press pressure of 7 MPa, and then, using a cold isostatic pressing (CIP) device, the CIP molding was conducted at a CIP pressure of 12 MPa. The preliminary sintering step was conducted on this CIP molded body at 600° C. for 5 hours in an air atmosphere so as to obtain a preliminary sintered body.

This preliminary sintered body was heated from room temperature to 860° C. at a fixed rate for 6 hours in a helium gas atmosphere, and the temperature was held there for 8 hours. It was then raised to 1080° C. at a fixed rate for 2 hours and held there for 2 hours. The temperature was then lowered by furnace cooling to a predetermined taking-out temperature of 100° C., and the sintered body was taken out. The bulk density of the sintered body was 3.02 g/cm³ (true density of 3.16 g/cm³ and relative density of 95.6%). It was rather light, but the sintering state thereof was not unusual in appearance.

Any of the evaluation results of the neutron moderation performance and mechanical strengths were good as shown in Table 2.

Example 9

The same $MgF_2$ powder was mixed with the same $CaF_2$ powder of 50% by weight as those in the above Example 2 and mixed using a ball mill for 12 hours. Thereafter, a CMC solution of 1% by weight was added thereto as a sintering aid. The compound was mixed in a pot mill for 12 hours so as to obtain a starting raw material. Using a uniaxial press device, the press molding was conducted at a press pressure of 30 MPa, and then, using a cold isostatic pressing (CIP) device, the CIP molding was conducted at a CIP pressure of 30 MPa. The preliminary sintering step was conducted on this CIP molded body at 610° C. for 7 hours in an air atmosphere so as to obtain a preliminary sintered body.

This preliminary sintered body was heated from room temperature to 860° C. at a fixed rate for 6 hours in a nitrogen gas atmosphere, and the temperature was held there for 8 hours. It was then raised to 970° C. at a fixed rate for 2 hours and held there for 4 hours. The temperature was then lowered by furnace cooling to a predetermined taking-out temperature of 100° C., and the sintered body was taken out. The bulk density of the sintered body was 3.00 g/cm³ (true density of 3.16 g/cm³ and relative density of 94.9%). It was somewhat light, but the sintering state thereof was not unusual in appearance.

Any of the evaluation results of the neutron moderation performance and mechanical strengths were good as shown in Table 2.

Example 10

The same $MgF_2$ powder was mixed with the same $CaF_2$ powder of 75% by weight as those in the above Example 1 and mixed using a ball mill for 12 hours. Thereafter, SAC of 0.07% by weight was added thereto as a sintering aid. The compound was mixed in a pot mill for 12 hours so as to obtain a starting raw material. Using a uniaxial press device, the press molding was conducted at a press pressure of 8 MPa, and then, using a cold isostatic pressing (CIP) device, the CIP molding was conducted at a CIP pressure of 10 MPa. The preliminary sintering step was conducted on this CIP molded body at 650° C. for 5 hours in an air atmosphere so as to obtain a preliminary sintered body.

This preliminary sintered body was heated from room temperature to 880° C. at a fixed rate for 6 hours in a nitrogen gas atmosphere, and the temperature was held there for 8 hours. It was then raised to 1060° C. at a fixed rate for 2 hours and held there for 3 hours. The temperature was then lowered by furnace cooling to a predetermined taking-out temperature of 100° C., and the sintered body was taken out. The bulk density of the sintered body was 3.02 g/cm³ (true density of 3.17 g/cm³ and relative density of 95.3%). It was somewhat light, but the sintering state thereof was not unusual in appearance.

Any of the evaluation results of the neutron moderation performance and mechanical strengths were good as shown in Table 2.

Example 11

The same $MgF_2$ powder was mixed with the same $CaF_2$ powder of 88% by weight as those in the above Example 6 and mixed using a ball mill for 12 hours. Thereafter, a CMC solution of 1% by weight was added thereto as a sintering aid. The compound was mixed in a pot mill for 12 hours so as to obtain a starting raw material. Using a uniaxial press device, the press molding was conducted at a press pressure of 30 MPa, and then, using a cold isostatic pressing (CIP) device, the CIP molding was conducted at a CIP pressure of 30 MPa. The preliminary sintering step was conducted on this CIP molded body at 650° C. for 5 hours in an air atmosphere so as to obtain a preliminary sintered body.

This preliminary sintered body was heated from room temperature to 880° C. at a fixed rate for 6 hours in a nitrogen gas atmosphere, and the temperature was held there for 8 hours. It was then raised to 950° C. at a fixed rate for 2 hours and held there for 4 hours. The temperature was then lowered by furnace cooling to a predetermined taking-out temperature of 100° C., and the sintered body was taken out. The bulk density of the sintered body was 3.01 g/cm³ (true density of 3.17 g/cm³ and relative density of 95.0%). It was somewhat light, but the sintering state thereof was not unusual in appearance.

Any of the evaluation results of the neutron moderation performance and mechanical strengths were good as shown in Table 2.

Example 12

The same $MgF_2$ powder was mixed with the same $CaF_2$ powder of 88% by weight as those in the above Example 1 and mixed using a ball mill for 12 hours. Thereafter, a CMC solution of 1% by weight was added thereto as a sintering aid. The compound was mixed in a pot mill for 12 hours so as to obtain a starting raw material. Using a uniaxial press device, the press molding was conducted at a press pressure of 8 MPa, and then, using a cold isostatic pressing (CIP) device, the CIP molding was conducted at a CIP pressure of 10 MPa. The preliminary sintering step was conducted on this CIP molded body at 650° C. for 5 hours in an air atmosphere so as to obtain a preliminary sintered body.

This preliminary sintered body was heated from room temperature to 880° C. at a fixed rate for 6 hours in a helium gas atmosphere, and the temperature was held there for 8 hours. It was then raised to 1120° C. at a fixed rate for 2 hours and held there for 2 hours. The temperature was then lowered by furnace cooling to a predetermined taking-out temperature of 100° C., and the sintered body was taken out. The bulk density of the sintered body was 3.04 g/cm$^3$ (true density of 3.17 g/cm$^3$ and relative density of 95.9%), and the sintering state thereof was not unusual in appearance.

Any of the evaluation results of the neutron moderation performance and mechanical strengths were good as shown in Table 2.

Comparative Example 1

A $MgF_2$ powder being a main raw material (mean particle diameter of 8 μm and purity of 99.9% by weight) was mixed with a $CaF_2$ powder (mean particle diameter of 8 μm and purity of 99.9% by weight) of 1.5% by weight, and mixed using a ball mill for 12 hours. Thereafter, SAC of 0.07% by weight was added thereto as a sintering aid. The compound was mixed in a pot mill for 12 hours so as to obtain a starting raw material.

In a similar manner to the above Example 1, using a uniaxial press device, the press molding was conducted at a press pressure of 20 MPa, and then, using a cold isostatic pressing (CIP) device, the CIP molding was conducted at a CIP pressure of 20 MPa. The preliminary sintering step was conducted on this CIP molded body at 550° C. for 8 hours in an air atmosphere so as to obtain a preliminary sintered body.

This preliminary sintered body was heated from room temperature to 670° C. at a fixed rate for 6 hours in a nitrogen gas atmosphere, and the temperature was held there for 6 hours. It was then raised to 1200° C. at a fixed rate for 2 hours and held there for 2 hours. The temperature was then lowered by furnace cooling to a predetermined taking-out temperature of 100° C., and the sintered body was taken out.

The bulk density of the sintered body was 2.93 g/cm$^3$ (true density of 3.15 g/cm$^3$ and relative density of 93.0%), which was light. When observing the inside of the sintered body, there were a myriad of large bubbles of 0.1 mm or more in diameter. It was considered that these large bubbles were aggregates of fine foaming bubbles, or those of foaming bubbles and residual bubbles since the high mix proportion of 12% by weight of the $MgF_2$ powder having a low melting point and heating at a high temperature of 1200° C. in the last sintering step allowed foaming to easily occur.

Some insufficient levels of neutron moderation performance and mechanical strengths were noticed.

Comparative Example 2

A $MgF_2$ powder being a main raw material (mean particle diameter of 10 μm and purity of 99.9% by weight) was mixed with a $CaF_2$ powder (mean particle diameter of 10 μm and purity of 99.9% by weight) of 0.2% by weight, and a starting raw material was prepared in a similar manner to the Comparative Example 1.

Using a uniaxial press device, the press molding was conducted at a press pressure of 4 MPa, and then, the CIP molding was conducted on this press molded body at a molding pressure of 4 MPa so as to obtain a CIP molded body in a similar manner to the Example 1. The preliminary sintering step was conducted on this CIP molded body at 600° C. for 6 hours in an air atmosphere so as to obtain a preliminary sintered body.

This preliminary sintered body was heated from room temperature to 830° C. at a fixed rate for 6 hours in a nitrogen gas atmosphere, and the temperature was held there for 5 hours. It was then raised to 950° C. at a fixed rate for 2 hours and held there for 4 hours. The temperature was then lowered by furnace cooling to a predetermined taking-out temperature of 100° C., and the sintered body was taken out.

The bulk density of the sintered body was 2.90 g/cm$^3$ (true density of 3.15 g/cm$^3$ and relative density of 92.1%), which was relatively light. This sintered body was soaked in pure water colored with a small quantity of ink solution for about 1 hour, and after raising it therefrom, the broken-cross section thereof was observed. The periphery portion thereof was wholly colored with this ink solution. It was considered that due to insufficient sintering, a large number of open pores were left.

Some insufficient levels of neutron moderation performance and mechanical strengths were noticed.

Comparative Example 3

A $MgF_2$ powder being a main raw material (mean particle diameter of 12 μm and purity of 99.9% by weight) was mixed with a $CaF_2$ powder (mean particle diameter of 12 μm and purity of 99.9% by weight) of 5% by weight, and mixed using a ball mill for 12 hours. Thereafter, a CMC solution of 1.0% by weight was added thereto as a sintering aid. The compound was mixed in a pot mill for 12 hours so as to obtain a starting raw material.

In a similar manner to the Example 1, using a uniaxial press device, the press molding was conducted at a press pressure of 20 MPa, and then, the CIP molding was conducted on this press molded body at a molding pressure of 20 MPa so as to obtain a CIP molded body. The preliminary sintering step was conducted on this CIP molded body at 700° C. for 10 hours in an air atmosphere so as to obtain a preliminary sintered body.

This preliminary sintered body was heated from room temperature to 900° C. at a fixed rate for 6 hours in a nitrogen gas atmosphere, and the temperature was held there for 10 hours. It was then raised to 1200° C. at a fixed rate for 2 hours and held there for 4 hours. The temperature was then lowered by furnace cooling to a predetermined taking-out temperature of 100° C., and the sintered body was taken out.

In part of the periphery portion of the sintered body, peeling was noticed. It was considered that this peeling was caused since foaming bubbles and residual bubbles gathered in the periphery portion and part of the periphery portion was cracked by the internal pressure of the bubbles. Here, since some part of the sintered body lost its shape, the bulk density thereof could not be measured.

Comparative Example 4

The same $MgF_2$ powder was mixed with the same $CaF_2$ powder of 5% by weight as those in the above Comparative Example 1, and a starting raw material was prepared in a similar manner thereto. Using a uniaxial press device, the press molding was conducted at a press pressure of 3 MPa, and then, this press molded body was CIP molded at a molding pressure of 3 MPa so as to obtain a CIP molded body in a similar manner to the above Example 1. The preliminary sintering step was conducted on this CIP molded body at 600° C. for 6 hours in an air atmosphere so as to obtain a preliminary sintered body.

This preliminary sintered body was heated from room temperature to 900° C. at a fixed rate for 6 hours in a nitrogen gas atmosphere, and the temperature was held there for 5 hours. It was then raised to 1200° C. at a fixed rate for 2 hours and held there for 2 hours. The temperature was then lowered by furnace cooling to a predetermined taking-out temperature of 100° C., and the sintered body was taken out.

Since there was a broken part in the periphery edge portion of the sintered body, the obtained bulk density thereof was an approximate value of about 2.92 g/cm$^3$ (true density of 3.15 g/cm$^3$ and relative density of 92.7%).

Some insufficient levels of neutron moderation performance and mechanical strengths were noticed.

Comparative Example 5

The same $MgF_2$ powder was mixed with the same $CaF_2$ powder of 25% by weight as those in the above Comparative Example 1, and a starting raw material was prepared in a similar manner thereto. Using a uniaxial press device, the press molding was conducted at a press pressure of 30 MPa, and then, this press molded body was CIP molded at a molding pressure of 30 MPa so as to obtain a CIP molded body in a similar manner to the Example 1. The preliminary sintering step was conducted on this CIP molded body at 550° C. for 8 hours in an air atmosphere so as to obtain a preliminary sintered body.

This preliminary sintered body was heated from room temperature to 870° C. at a fixed rate for 6 hours in a nitrogen gas atmosphere, and the temperature was held there for 6 hours. It was then raised to 1160° C. at a fixed rate for 2 hours and held there for 3 hours. The temperature was then lowered by furnace cooling to a predetermined taking-out temperature of 100° C., and the sintered body was taken out. The bulk density of the sintered body was 2.93 g/cm$^3$ (true density of 3.15 g/cm$^3$ and relative density of 93.0%).

Some insufficient levels of neutron moderation performance and mechanical strengths were noticed.

Comparative Example 6

The same $MgF_2$ powder was mixed with the same $CaF_2$ powder of 25% by weight as those in the above Comparative Example 1, and a starting raw material was prepared in a similar manner thereto. Using a uniaxial press device, the press molding was conducted at a press pressure of 4 MPa, and then, this press molded body was CIP molded at a molding pressure of 4 MPa so as to obtain a CIP molded body in a similar manner to the above Example 1. The preliminary sintering step was conducted on this CIP molded body at 600° C. for 6 hours in an air atmosphere so as to obtain a preliminary sintered body.

This preliminary sintered body was heated from room temperature to 830° C. at a fixed rate for 6 hours in a nitrogen gas atmosphere, and the temperature was held there for 5 hours. It was then raised to 950° C. at a fixed rate for 2 hours and held there for 4 hours. The temperature was then lowered by furnace cooling to a predetermined taking-out temperature of 100° C., and the sintered body was taken out. The bulk density of the sintered body was 2.91 g/cm$^3$ (true density of 3.15 g/cm$^3$ and relative density of 92.4%).

Some insufficient levels of neutron moderation performance and mechanical strengths were noticed.

Comparative Example 7

The same $MgF_2$ powder was mixed with the same $CaF_2$ powder of 50% by weight as those in the above Comparative Example 1, and a starting raw material was prepared in a similar manner thereto. Using a uniaxial press device, the press molding was conducted at a press pressure of 20 MPa, and then, this press molded body was CIP molded at a molding pressure of 20 MPa so as to obtain a CIP molded body in a similar manner to the Example 1. The preliminary sintering step was conducted on this CIP molded body at 550° C. for 8 hours in an air atmosphere so as to obtain a preliminary sintered body.

This preliminary sintered body was heated from room temperature to 880° C. at a fixed rate for 6 hours in a nitrogen gas atmosphere, and the temperature was held there for 5 hours. It was then raised to 1200° C. at a fixed rate for 2 hours and held there for 2 hours. The temperature was then lowered by furnace cooling to a predetermined taking-out temperature of 100° C., and the sintered body was taken out.

The bulk density of the sintered body was 2.91 g/cm$^3$ (true density of 3.16 g/cm$^3$ and relative density of 92.1%).

Some insufficient levels of neutron moderation performance and mechanical strengths were noticed.

Comparative Example 8

The same $MgF_2$ powder was mixed with the same $CaF_2$ powder of 50% by weight as those in the above Comparative Example 1, and a starting raw material was prepared in a similar manner thereto. Using a uniaxial press device, the press molding was conducted at a press pressure of 4 MPa, and then, this press molded body was CIP molded at a molding pressure of 4 MPa so as to obtain a CIP molded body in a similar manner to the Example 1. The preliminary sintering step was conducted on this CIP molded body at 600° C. for 6 hours in an air atmosphere so as to obtain a preliminary sintered body.

This preliminary sintered body was heated from room temperature to 850° C. at a fixed rate for 6 hours in a nitrogen gas atmosphere, and the temperature was held there for 5 hours. It was then raised to 960° C. at a fixed rate for 2 hours and held there for 4 hours. The temperature was then lowered by furnace cooling to a predetermined taking-out temperature of 100° C., and the sintered body was taken out.

The bulk density of the sintered body was 2.92 g/cm$^3$ (true density of 3.16 g/cm$^3$ and relative density of 92.4%).

Some insufficient levels of neutron moderation performance and mechanical strengths were noticed.

Comparative Example 9

The same $MgF_2$ powder was mixed with the same $CaF_2$ powder of 88% by weight as those in the above Comparative Example 1, and a starting raw material was prepared in a similar manner thereto. Using a uniaxial press device, the press molding was conducted at a press pressure of 20 MPa, and then, this press molded body was CIP molded at a molding pressure of 20 MPa so as to obtain a CIP molded body in a similar manner to the Example 1. The preliminary sintering step was conducted on this CIP molded body at 530° C. for 8 hours in an air atmosphere so as to obtain a preliminary sintered body.

This preliminary sintered body was heated from room temperature to 900° C. at a fixed rate for 6 hours in a nitrogen gas atmosphere, and the temperature was held there for 6 hours. It was then raised to 1160° C. at a fixed rate for 2 hours and held there for 4 hours. The temperature was then lowered by furnace cooling to a predetermined taking-out temperature of 100° C., and the sintered body was taken out.

The bulk density of the sintered body was 2.90 g/cm³ (true density of 3.17 g/cm³ and relative density of 91.5%).

Some insufficient levels of neutron moderation performance and mechanical strengths were recognized.

Comparative Example 10

The same $MgF_2$ powder was mixed with the same $CaF_2$ powder of 88% by weight as those in the above Comparative Example 1, and a starting raw material was prepared in a similar manner thereto. Using a uniaxial press device, the press molding was conducted at a press pressure of 4 MPa, and then, this press molded body was CIP molded at a molding pressure of 4 MPa so as to obtain a CIP molded body in a similar manner to the Example 1. The preliminary sintering step was conducted on this CIP molded body at 600° C. for 6 hours in an air atmosphere so as to obtain a preliminary sintered body.

This preliminary sintered body was heated from room temperature to 860° C. at a fixed rate for 6 hours in a nitrogen gas atmosphere, and the temperature was held there for 6 hours. It was then raised to 970° C. at a fixed rate for 2 hours and held there for 5 hours. The temperature was then lowered by furnace cooling to a predetermined taking-out temperature of 100° C., and the sintered body was taken out.

The bulk density of the sintered body was 2.93 g/cm³ (true density of 3.17 g/cm³ and relative density of 92.4%).

Some insufficient levels of neutron moderation performance and mechanical strengths were noticed.

Comparative Example 11

The same $MgF_2$ powder was mixed with the same $CaF_2$ powder of 3% by weight as those in the above Comparative Example 1, and a starting raw material was prepared in a similar manner thereto. Using a uniaxial press device, the press molding was conducted at a press pressure of 30 MPa, and then, this press molded body was CIP molded at a molding pressure of 30 MPa so as to obtain a CIP molded body. The preliminary sintering step was conducted on this CIP molded body at 660° C. for 8 hours in an air atmosphere so as to obtain a preliminary sintered body.

This preliminary sintered body was heated from room temperature to 1060° C. at a fixed rate for 6 hours in a nitrogen gas atmosphere, and the temperature was held there for 2 hours. The temperature was then lowered by furnace cooling to a predetermined taking-out temperature of 100° C., and the sintered body was taken out.

The sintering step was conducted only in one stage (only the secondary sintering of the primary and secondary sintering was conducted). The bulk density of the sintered body was 2.93 g/cm³ (true density of 3.15 g/cm³ and relative density of 93.0%).

Some insufficient levels of neutron moderation performance and mechanical strengths were noticed.

Comparative Example 12

The same $MgF_2$ powder was mixed with the same $CaF_2$ powder of 25% by weight as those in the above Comparative Example 1, and a starting raw material was prepared in a similar manner thereto. Using a uniaxial press device, the press molding was conducted at a press pressure of 30 MPa, and then, this press molded body was CIP molded at a molding pressure of 30 MPa so as to obtain a CIP molded body. The preliminary sintering step was conducted on this CIP molded body at 650° C. for 6 hours in an air atmosphere so as to obtain a preliminary sintered body.

This preliminary sintered body was heated from room temperature to 1150° C. at a fixed rate for 6 hours in a nitrogen gas atmosphere, and the temperature was held there for 1.5 hours. The temperature was then lowered by furnace cooling to a predetermined taking-out temperature of 100° C., and the sintered body was taken out.

The sintering step was conducted only in one stage (only the secondary sintering of the primary and secondary sintering was conducted). The bulk density of the sintered body was 2.90 g/cm³ (true density of 3.15 g/cm³ and relative density of 92.1%).

Some insufficient levels of neutron moderation performance and mechanical strengths were noticed.

[Comparative Material 1]

Using the same powder of $MgF_2$ simple as that in the above Example 6, a starting raw material was prepared in a similar manner to the Example 1. In a similar manner to the Example 1, using a uniaxial press device, the press molding was conducted at a press pressure of 20 MPa, and then, this press molded body was CIP molded at a molding pressure of 20 MPa so as to obtain a CIP molded body. The preliminary sintering step was conducted on this CIP molded body at 600° C. for 6 hours in an air atmosphere so as to obtain a preliminary sintered body.

This preliminary sintered body was heated from room temperature to 840° C. at a fixed rate for 6 hours in a nitrogen gas atmosphere, and the temperature was held there for 6 hours. It was then raised to 1100° C. at a fixed rate for 2 hours and held there for 2 hours. The temperature was then lowered by furnace cooling to a predetermined taking-out temperature of 100° C., and the sintered body was taken out.

The bulk density of the sintered body was 2.97 g/cm³ (true density of 3.15 g/cm³ and relative density of 94.3%).

The neutron moderation performance of the sintered body was good enough to compare favorably with the Examples as shown in Table 2. On the other hand, the mechanical strengths thereof were within a range of good levels as shown in Table 2, but equivalent to the lower levels of strengths in the Examples. For information, this Comparative Material 1 is equivalent to a sintered body according to the prior application.

[Comparative Material 2]

Using the same $CaF_2$ powder being a secondary raw material as that in the Example 6, a starting raw material was prepared in a similar manner to the Example 6. In a similar manner to the Example 1, using a uniaxial press device, the press molding was conducted at a press pressure of 20 MPa, and then, this press molded body was CIP molded at a molding pressure of 20 MPa so as to obtain a CIP molded body. The preliminary sintering step was conducted on this CIP molded body at 600° C. for 6 hours in an air atmosphere so as to obtain a preliminary sintered body.

This preliminary sintered body was heated from room temperature to 880° C. at a fixed rate for 6 hours in a nitrogen gas atmosphere, and the temperature was held there for 6 hours. It was then raised to 1130° C. at a fixed rate for 2 hours and held there for 2 hours. The temperature was then lowered by furnace cooling to a predetermined taking-out temperature of 100° C., and the sintered body was taken out.

The bulk density of the sintered body was 3.00 g/cm³ (true density of 3.18 g/cm³ and relative density of 94.3%).

The mechanical strengths of the sintered body were good, while some insufficient levels of neutron moderation performance were noticed.

The invention claimed is:

1. A $MgF_2$—$CaF_2$ binary system sintered body for a radiation moderator, comprising $MgF_2$ containing $CaF_2$ from 1.5% by weight to 80% by weight inclusive, having a compact polycrystalline structure with a bulk density of 2.96 g/cm$^3$ or more and having radiation moderation performance.

2. The $MgF_2$—$CaF_2$ binary system sintered body for a radiation moderator according to claim 1, wherein the radiation moderation performance is neutron moderation performance.

3. The $MgF_2$—$CaF_2$ binary system sintered body for a radiation moderator according to claim 1, having a bending strength of 15 MPa or more and a Vickers hardness of 90 or more as regards mechanical strengths.

4. A method for producing the $MgF_2$—$CaF_2$ binary system sintered body for a radiation moderator according to claim 1, comprising the steps of:
mixing a $MgF_2$ powder with a $CaF_2$ powder of 1.5-80% by weight and further adding 0.02-1% by weight of a sintering aid thereto to mix;
molding the raw material powder compounded in the preceding step at a molding pressure of 5 MPa or more using a press molding device;
molding the press molded article at a molding pressure of 5 MPa or more using a cold isostatic pressing (CIP) device;
conducting preliminary sintering by heating the CIP molded article in a temperature range of 600° C.-700° C. in an air atmosphere;
conducting sintering by heating in a temperature range from (Tn-100)° C. to (Tn)° C. when the starting temperature of foaming of the preliminary sintered body is (Tn)° C., in an air atmosphere or in an inert gas atmosphere; and
forming a sintered body having a compact structure by heating in a temperature range of 900° C.-1150° C. in the same atmosphere as the preceding step.

5. The method for producing a $MgF_2$—$CaF_2$ binary system sintered body for a radiation moderator according to claim 4,
wherein the shape of a particle size distribution curve of the compound shows a sub-1-peak-type or 1-peak-type particle size distribution, the maximum particle diameter is 50 μm or less and the median diameter of the particles is 6 μm or less.

6. The method for producing a $MgF_2$—$CaF_2$ binary system sintered body for a radiation moderator according to claim 4,
wherein the inert gas atmosphere in the sintering step comprises one kind of gas or a mixture of plural kinds of gases, selected from among nitrogen, helium, argon and neon.

7. The method for producing a $MgF_2$—$CaF_2$ binary system sintered body for a radiation moderator according to claim 5,
wherein the inert gas atmosphere in the sintering step comprises one kind of gas or a mixture of plural kinds of gases, selected from among nitrogen, helium, argon and neon.

* * * * *